(12) United States Patent
Rastaldi

(10) Patent No.: US 8,673,851 B2
(45) Date of Patent: Mar. 18, 2014

(54) SYNAPSE-SPECIFIC PROTEINS IN GLOMERULI

(75) Inventor: Maria P. Rastaldi, Rho (IT)

(73) Assignee: Fondazione d'Amico per la Ricerca Sulle Malattie Renali, Milan (IT)

(*) Notice: Subject to any disclaimer, the term of this patent is extended or adjusted under 35 U.S.C. 154(b) by 272 days.

(21) Appl. No.: 11/963,353

(22) Filed: Dec. 21, 2007

(65) Prior Publication Data

US 2008/0214458 A1 Sep. 4, 2008

Related U.S. Application Data

(63) Continuation of application No. PCT/IB2006/002746, filed on Jul. 3, 2006, and a continuation-in-part of application No. PCT/IB2006/002764, filed on Jun. 30, 2006.

(30) Foreign Application Priority Data

Jul. 1, 2005 (GB) .................................. 0513553.8

(51) Int. Cl.
 *A61K 38/18* (2006.01)
 *A61K 35/22* (2006.01)
 *C07K 14/475* (2006.01)
 *A61P 13/12* (2006.01)

(52) U.S. Cl.
 USPC .......... 514/7.6; 514/15.4; 424/198.1; 424/558

(58) Field of Classification Search
 None
 See application file for complete search history.

(56) References Cited

U.S. PATENT DOCUMENTS

2002/0091128 A1* 7/2002 Mylari ..................... 514/252.14

OTHER PUBLICATIONS

Wellmer et al., Journal of the Peripheral Nervous System, 6:204-210, Dec. 2001.*
Petereit et al., Multiple Sclerosis, 30:16-20, 2003.*
Oderfeld-Nowak et al., Neuroscience Letters, 308:165-168, 2001.*
Ikenouchi et al. Progress in Neuro-psychopharm and Biol Psychiatry, 30:1359-1363, 2006.*
Huber et al., Development Biology, 179: 369-381, 1996.*
Hladunewich et al., Clin J Am Soc Nephrol, 4:1417-1422, 2009.*
Bek et al., Dopamine depolarizes podoctyes via a D1-like receptor. Nephrology, Dialysis, Transplantation: Official Publication of the European Renal Association. 14:631-509 (1999).
Cohen et al., Tumorigenicity of sodium ascorbate in male rats. *Cancer Research*. 58:2557-61 (1998).
Kasselman et al., BDNF: a missing link between sympathetic dysfunction and inflammatory disease? *J Neuroimmunol*. 175:118-27 (2006).
Mattson et al., A neural signaling triumvirate that influences ageing and age-related disease: insulin/IGF-1, BDNF and serotonin. *Ageing Res Rev.* 3:445-64 (2004).
Nitschke et al., Angiotensin II increases the intracellular calcium activity in podocytes of the intact glomerulus. *Kidney International.* 57:41-9 (2000).
Rastaldi et al., Glomerular podocytes possess the synaptic vesicle molecule Rab3A and its specific effector rabphilin-3a. *The American Journal of Pathology.* 163:889-99 (2003).
Schluter et al., Localization versus function of Rab3 proteins. Evidence for a common regulatory role in controlling fusion. *J. Biol. Chem.* 277:40919-29 (2002).
Simons et al., Direct membrane transport is involved in process formation in cultured podocytes. *J. Amer. Soc. Nephrol.* 10:1633-9 (1999).
Zerial et al., Rab proteins as membrane organizers. *Nat Rev Mol Cell Biol.* 2:107-17 (2001).
PCT Search Report, PCT/IB2006/002746, Jun. 23, 2008.
PCT Written Opinion, PCT/IB2006/002746, Jun. 23, 2008.
International Preliminary Report on Patentability, PCT/IB2006/002746, Jun. 23, 2008.

* cited by examiner

*Primary Examiner* — Jeffrey Stucker
*Assistant Examiner* — Stacey N MacFarlane
(74) *Attorney, Agent, or Firm* — Marshall, Gerstein & Borun LLP

(57) ABSTRACT

The present invention identifies that glomeruli express many neuron-specific and especially synapse-specific protein similarities. In particular, the present invention identifies Rab3A expression, including the expression of altered forms, as well as expression of other synapse-specific proteins including neurotransmitter receptors. The invention further identifies that modulation of the activity of these synapse-specific proteins results in modulation of podocytes.

4 Claims, 37 Drawing Sheets

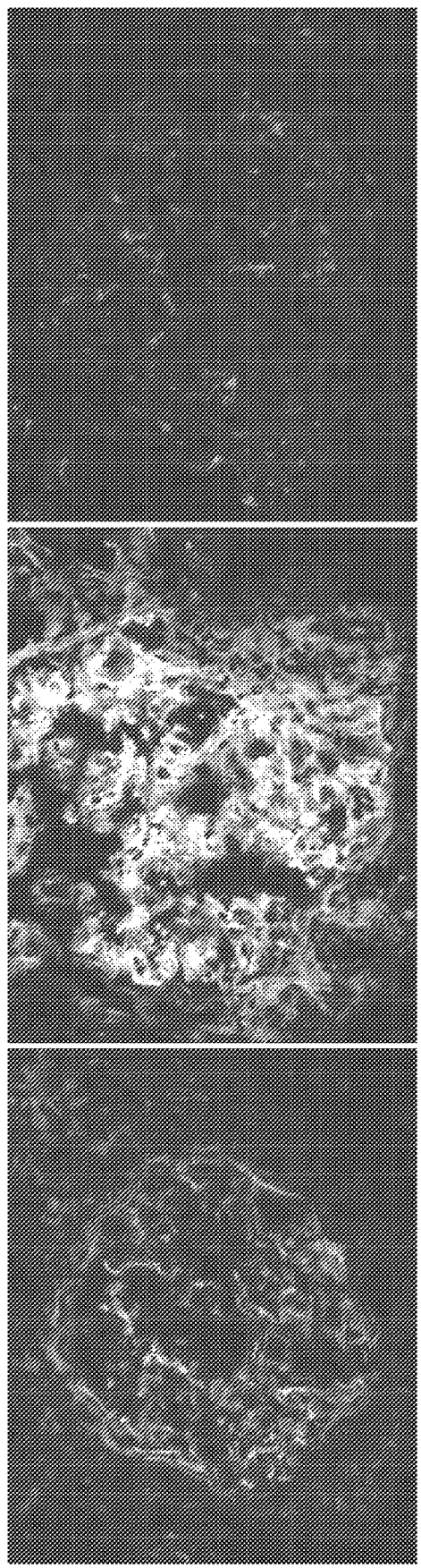

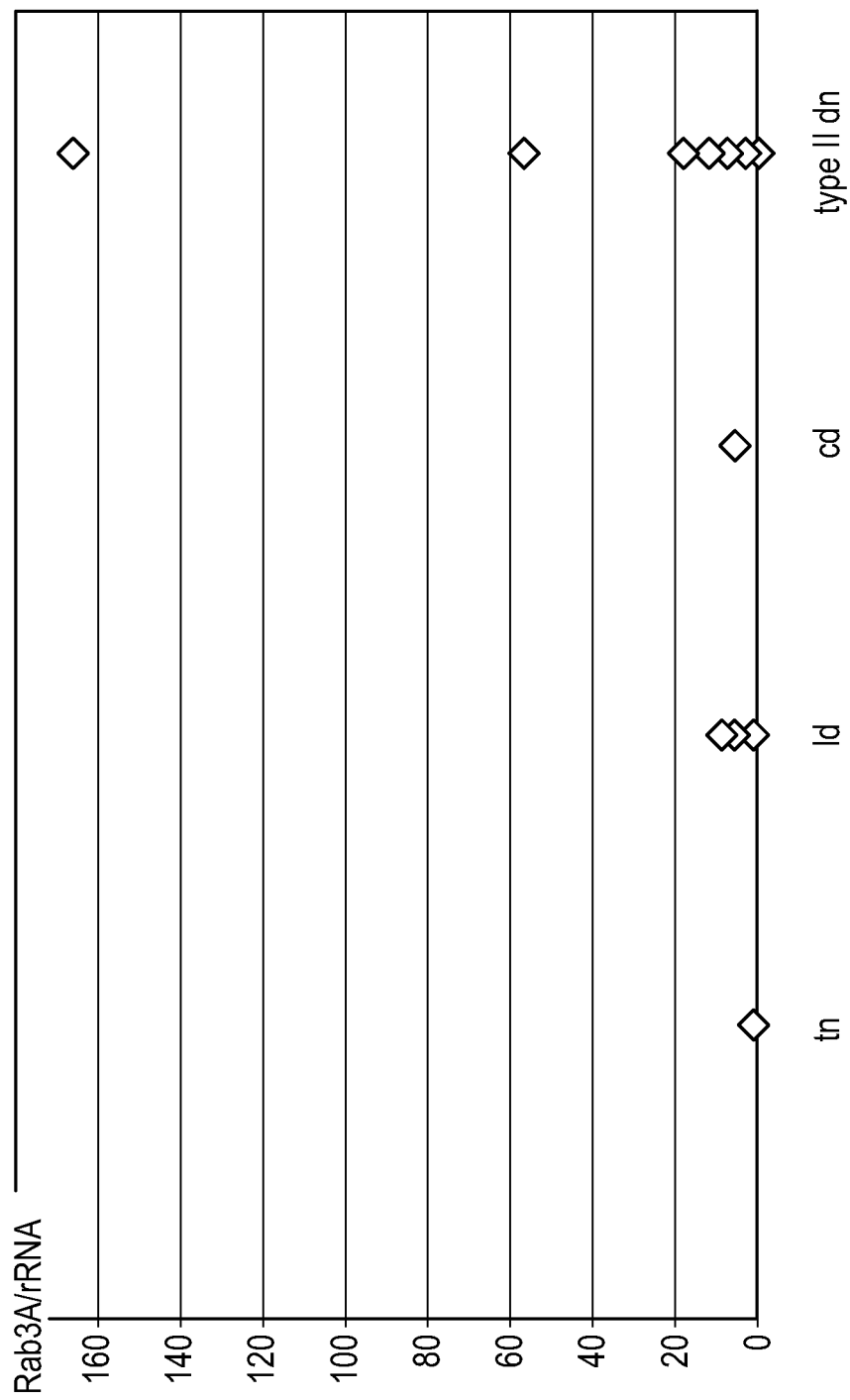

| Location | NT Shift | AA position | Number of cases and zygosity | Contig | Position on the sequence | SNP Data-base |
|---|---|---|---|---|---|---|
| Intron 4 | T → C | | 3 CT<br>11 CC | 9571310 | 22516 | db8109807 |
| Intron 4 | A → C | | 18 AC<br>13 CC | 9571771 | 22977 | db12462801 |
| Intron 4 | G → A | | 1 GA | 9571780 | 23067 | - |
| Intron 4 | T → A | | 1 AT | 9571939 | 23145 | - |
| Intron 4 | A → G | | 16 AG<br>23 GG | 9572167 | 23373 | db2271882 |
| Intron 4 | G → A | | 2 GA | 9572232 | 23438 | - |
| Exon 3 | C → T | AA 143<br>Arg → Gln | 1 CT | 9572381 | 23587 | - |
| Intron 3 | C → A | | 1 CA | 9572489 | 23695 | - |
| Intron 3 | A → G | | 3 AG | 9573913 | 25119 | db3803919 |
| Exon 2 | A → G | AA95<br>No change | 3 AG | 9574001 | 25207 | db1046565 |
| Exon 1 | G → T | AA66<br>Arg → Ser | 1 GT | 9576157 | 27363 | - |
| Intron 1 | C → T | | 19 CT<br>4 TT | 9576614 | 27819 | db4808119 |
| Intron 1 | C → A | | 1 CA | 9576615 | 27820 | - |
| Intron 1 | G → A | | 1 GA | 9576722 | 27927 | - |

*FIG. 2f*

SYNAPSE-SPECIFIC PROTEINS IN GLOMERULI

This application is a continuation of International Patent Application No. PCT/IB2006/002746, filed 3 Jul. 2006, and a continuation-in-part of International Application No. PCT/IB2006/002764, filed 30 Jun. 2006; and both of said international applications claim priority benefit of Great Britain Application No. 0513553.8, filed 1 Jul. 2005. All of these priority applications are incorporated herein by reference in their entireties.

FIELD OF INVENTION

The present invention identifies that glomeruli express many neuron-specific and especially synapse-specific protein similarities. Accordingly, the present invention relates to methods of treating glomeruli through interaction with synapse-specific proteins and neurotransmitter receptors. The present invention also relates to the finding that Rab3A is altered in proteinuric diseases and variants of the molecule can be found in human nephropathies. Accordingly, the present invention relates to methods for diagnosing and treating proteinuric or glomerular disease as well as to methods for identifying compounds that can be used in such treatments.

BACKGROUND OF INVENTION

Podocytes are the visceral epithelial cells of the kidney glomerulus. They have elaborate long, regularly spaced, interdigitated foot processes that completely enwrap the glomerular capillaries. Interdigitating podocyte foot processes form an ~40-nm-wide filtration slit occupied by a continuous membrane-like structure called the slit diaphragm.

Podocytes are highly differentiated cells with a crucial role in the glomerular filtration barrier. When podocytes are injured, the intercellular junctions and cytoskeletal structure of the foot processes are altered and the cell takes on an "effaced" phenotype. Typical slit diaphragm structures disappear and proteinuria develops.

Proteinuria describes a condition in which urine contains an abnormal amount of protein. Proteinuria can result from inflammatory, metabolic, immunologic or genetic causes. Proteinuric diseases are either primary or secondary and can occur during systemic diseases, such as hypertension, diabetes, systemic lupus erythematosus (SLE). Examples of renal glomerular diseases are IgA nephropathy, Focal segmental glomerulosclerosis (FSGS), Membranous nephropathy and Minimal change disease (MCD), Goodpasture's syndrome, Hereditary Nephritis-Alport Syndrome, Infection-related Glomerular Disease (Acute post-streptococcal glomerulonephritis (PSGN), Bacterial endocarditis, HIV), etc.

In most cases, primary glomerulonephritis stands for a disease of still unknown etiology, meaning that there remains an imperious need for improved methods for diagnosing and treating these diseases.

The properties and role of different proteins in podocytes is poorly understood. It was previously observed that glomerular podocytes possess Rab3A, a GTPase restricted to cell types capable of highly regulated exocytosis. However, to date, the role of Rab3A in disease has not been elucidated.

STATEMENT OF INVENTION

The present invention identifies that glomeruli express many neuron-specific and especially synapse-specific protein similarities. In particular, the present invention identifies Rab3A expression, including the expression of altered forms, as well as expression of other synapse-specific proteins including neurotransmitter receptors. The invention further identifies that modulation of the activity of these synapse-specific proteins results in modulation of podocytes.

Accordingly, in one aspect of the invention there is provided a modulator of a synapse-specific protein for use in the treatment of a nephropathy. Suitably, there is provided use of a modulator of a synapse-specific protein in the manufacture of a medicament for use in the treatment of a nephropathy.

By "synapse-specific" is meant a protein whose expression is normally associated with a synapse.

In one embodiment, the synapse-specific protein is selected from Rab3A, NMDA-1, synapsin-1, tetanus toxin receptor, BDNF-receptor and a GABA receptor. Other synapse-specific proteins will be familiar to the person skilled in the art.

Suitably the modulator is a modulator specific to the synapse-specific protein. In one embodiment the modulator is BDNF. Accordingly, in one embodiment there is provided the use of BDNF in the manufacture of a medicament for use in the treatment of nephropathy.

In another embodiment, the modulator is a modulator of the actin cytoskeleton. As shown herein, compounds such as norketamine hydrochloride which interact with NMDA and modify glutamate signalling for podocyte homeostasis, can cause a profound alteration of the actin cytoskeleton. Accordingly, suitable modulators include modulators of the glutamate signalling pathway such as glutamate.

The present application identifies a highly variable Rab3A expression in human nephropathies. Furthermore, the present application identifies variable forms of Rab3A and their association with nephropathy.

Accordingly, in one aspect of the invention there is provided a method for diagnosing nephropathy in an individual comprising detecting expression of Rab3A protein wherein altered expression in the individual compared to a control is indicative of nephropathy.

By "nephropathy" we include diseases resulting in disorders of the kidney. In particular, nephropathy refers to diseases characterised by alteration of glomerular cells, of the glomerular basement membrane, or of the renal interstitium. In particular, these diseases may be characterised by proteinuria which can result from inflammatory, metabolic, immunologic or genetic causes. Proteinuric diseases are either primary or secondary and can occur during systemic diseases, such as hypertension, diabetes, systemic lupus erythematosus (SLE). Examples of renal glomerular diseases are IgA nephropathy, Focal segmental glomerulosclerosis (FSGS), Membranous nephropathy and Minimal change disease (MCD), all of them occurring as primary or secondary, Goodpasture's syndrome, Hereditary Nephritis-Alport Syndrome, Infection-related Glomerular Disease (Acute post-streptococcal glomerulonephritis (PSGN), Bacterial endocarditis, HIV), etc.

By "altered expression" it is meant that expression may be either increased or decreased, compared to the expression in a control sample derived from a normal, non-diseased individual. Rab3A decrease has been found associated to a reduction of renal function.

Suitably, altered expression can include expression of an altered or mutated form of Rab3A.

Accordingly, in another aspect of the invention, there is provided a method for determining an individual's susceptibility to developing nephropathy comprising analysing the individual's Rab3A gene for at least one mutation in which a mutation in the gene indicates a susceptibility to developing nephropathy.

In another aspect, there is provided a method for diagnosing nephropathy comprising analysing the Rab3A gene for at least one coding or non-coding (exonic or intronic) mutation in which a mutation in the gene is indicative of nephropathy.

Suitably, the mutation in the Rab3A gene results in Arginine at position 66 of the corresponding amino acid sequence changing to another amino acid.

By "another amino acid" is meant a "non-Arginine" amino acid. Another amino acid may be a negatively charged amino acid such as aspartic acid and glutamic acid; a positively charged amino acid such as lysine; or an amino acid with an uncharged polar head group having similar hydrophilicity values such as leucine, isoleucine, valine, glycine, alanine, asparagine, glutamine, serine, threonine, phenylalanine, and tyrosine.

In one embodiment, the mutation in the Rab3A gene is at nucleotide 27363 of exon 1 in which G is mutated to T resulting in Arginine at position 66 of the corresponding amino acid sequence changing to Serine.

Where the mutation results in a change in Arginine at position 66, the nephropathy is preferably IgA nephropathy.

In another embodiment, the mutation in the Rab3A gene results in Arginine at position 143 of the corresponding amino acid sequence changing to another amino acid.

In a further embodiment, the mutation in the Rab3A gene is at nucleotide 23587 of exon 3 in which C is mutated to T resulting in Arginine at position 143 of the corresponding amino acid sequence changing to Glycine.

Where the mutation results in a change in Arginine at position 143, the nephropathy is preferably Lupus nephritis.

In yet another embodiment, the nucleic acid molecule encoding Rab3A has a truncation.

Suitably, the nucleic acid molecule encoding Rab3A has a truncation of 125 nucleotides producing a frame shift and an abnormal stop codon at nucleotide 361.

In one embodiment, a method in accordance with any embodiment of the invention comprises:
a) isolating a nucleic acid from a biological sample that has been removed from the patient; and
b) determining the nucleic acid sequence of the Rab3A gene or a portion thereof.

Suitably, the method of the invention comprises detecting any one of the nucleotide alterations identified in FIG. 2f.

Suitable methods for identifying the nucleotides present at each of these positions are described herein and include TaqMan, SNaPshot, allele-specific polymerase chain reaction amplification, allele refractory mutation system (ARMS), restriction fragment length polymorphism analysis and sequencing. Such methods can employ genotyping probes or oligonucleotides as described herein.

In a further embodiment, the method comprises:
a) isolating a protein from a biological sample that has been removed from the patient; and
b) detecting the presence of a Rab3A protein having a non-arginine amino acid at position 66 or 143.

A biological sample from a patient can include any DNA-containing biological material including blood or tissue extracts such as a buccal scrape. Typically a blood sample is used. DNA can be extracted for analysis from many types of biological samples for use in genotyping. For example, DNA is typically extracted from blood using commercial kits such as those available from Qiagen or Nucleon and PureGene (Flowgen) though it is feasible to determine a genotype directly from the blood sample.

In another aspect of the invention there is provided the use of a modulator of Rab3A for the preparation of a medicament for use in the treatment of glomerular diseases. In one embodiment the modulator is an inhibitor of inflammation. Glomerular disease can be related to inflammation.

Suitably inflammation of the glomeruli is characteristic of a nephropathy.

In a further aspect of the invention there is provided a method for identifying a candidate molecule for the treatment of glomerular diseases comprising: (a) providing a candidate molecule, (b) incubating the candidate molecule with Rab3A, and (c) detecting binding of the candidate molecule Rab3A wherein binding to Rab3A is indicative of a candidate molecule. Suitably said candidate molecule is a modulator of Rab3A.

In another aspect, there is provided a method for identifying a candidate molecule for treatment of glomerular diseases comprising a glutamate and/or a GABA uptake assay as described herein in the presence or absence of a candidate molecule. Suitably said candidate molecule is a modulator of Rab3A.

In a further aspect of the invention there is provided a method for identifying an inhibitor of inflammation in the glomeruli comprising: a) providing a candidate molecule, (b) incubating the candidate molecule with Rab3A, and (c) detecting binding of the candidate molecule Rab3A wherein binding to Rab3A is indicative of a candidate inhibitor.

In another aspect, there is provided a method for identifying an modulator or inhibitor of inflammation in the glomeruli comprising a glutamate and/or a GABA uptake assay as described herein in the presence or absence of a candidate molecule.

DETAILED DESCRIPTION OF THE INVENTION

The present invention is further described by way of example, and with reference to the following figures wherein:

FIG. 1 shows results from Rab3A null mice.

Panel a): Urinary Albumin to urinary Creatinine ratio (µg/mg) measured on 24 h urine samples in Rab3A wild type (wt) and knockout animals (ko) at different ages (8 animals per group). Values are given as mean±standard error.

Panels b)-e): Transmission electron microscopy of renal tissue from three month old wild type and Rab3A-ko animals. Compared to the normal cellularity (b) and integrity of podocyte foot processes (c) of the wild type, mesangial expansion and proliferation, associated to segmental foot process effacement, are present in the knock out (d). Foot process effacement is more evident at higher magnification (e) (uranyl acetate-lead citrate, 4600× (b, d), 17000× (c), 13000× (e)).

Panels f)-i): Nephrin (f, h) and podocin (g, i) glomerular labeling in three month old mice. Compared to the wild type (f, g), the Rab3A null animal (h, i) shows a segmental decreased expression of both podocyte proteins (indirect immunofluorescence, 400×).

Panel j)-m): Renal tissue from 6 month old mice: mesangial expansion is absent from glomeruli of a wild type mouse (j, k), whereas it is evident in the corresponding knock out (l, m), and its entity is better observed at higher magnification (Masson Trichrome, 100×, 200×). Panel n)-q): Tenascin C (n, p) and Collagen type I (o, q) stainings in six month old mice. Compared to the wild type (n, o), the knock out (p, q) shows increased glomerular positivity for both molecules (indirect immunofluorescence, 200×).

FIG. 2 shows Rab3A in human nephropathies.

Panels a)-e): Expression of Rab3A in human proteinuric diseases. By immunohistochemistry (a-c) it is evident the great variability of the molecule. Here, three cases of type II diabetic nephropathy alternatively show a comma-like staining along the glomerular basement membrane (a), or an increased (b) or a decreased labeling (c) (indirect immunofluorescence, 250×). The immunohistochemical expression levels of Rab3A (d), semiquantitatively evaluated in 101 renal tissues from patients with different proteinuric diseases [x axis, 0: absent (23 cases); 0.5: traces (13 cases); 1: regular comma-like positivity along the GBM (38 cases); 2: increased staining (26 cases)], highly correlate ($P<0.0001$, Pearson Correlation, two-tailed) with serum creatinine (mg/dl) levels at time of renal biopsy (y axis) expressed as mean±standard error. The dotted red line indicates the level of normal serum creatinine (1.4 mg/dl). By quantitative RT-PCR (e), the expression of Rab3A/rRNA is highly variable in glomeruli from type II diabetic nephropathy (type II dn) compared to the levels obtained from control kidneys (tn: tumor nephrectomies, ld: transplant living donors, cd: transplant cadaveric donors).

Panels f)-h): RAB3A SNPs detected in 50 DNA from patients with various nephropathies (f): besides already published SNPs, 6 sporadic intronic SNPs (circled in red) and 2 exonic SNPs (highlighted in yellow) have been found. The SNP found in exon 3 is shown (g). The amino acids involved in the exonic SNPs are represented on the molecule in panel h).

Panel i): A double band (arrow) is detectable by electrophoresis of Rab3A cDNA obtained from glomeruli of renal biopsies.

FIG. 3 shows Rab3A, glutamate, and glutamate receptors.

Panel a): Rab3A western blot analysis of immunoprecipitates. Line 1: normal mouse brain, Rab3A; line 2: normal mouse glomeruli, Rab3A; line 3: normal mouse glomeruli, rabbit IgG control; line 4: normal mouse glomeruli, negative control.

Panel b): By double staining (rab3A in green, glutamate in red), several scattered dots of positivity appear in yellow, indicating a colocalization of the molecules (mouse anti-Rab3A, goat anti-mouse Alexa Fluor 488; rabbit anti-glutamate, goat anti-rabbit Alexa Fluor 486; 450×).

Panel c), d): Normal mouse glomeruli are positive for glutamate (c) and glutamate metabotropic receptor 7 (d) with a pattern lining the glomerular basement membrane (indirect immunofluorescence on frozen semi-thin, 1 um thick, sections, 450×).

Panel e)-f): Normal human glomeruli stain positively for glutamate (e), and the glutamate receptor NMDA-1 (f) (indirect immunofluorescence, 250×).

Panel g): Western blot analysis for detection of NMDA-1 glutamate receptor in lysates of normal mouse glomeruli (line 1) and normal mouse brain (line 2). A band of approximately 100 kDa (arrow) is detectable in material from normal mouse glomeruli as well as from brain. Other bands are observable, those of higher molecular weight presumably due to polymers.

FIG. 4 shows glutamate release and uptake by podocytes.

Panel a): α-latrotoxin-stimulated glutamate release from cultured mouse podocytes. The graph shows the representative results from three experiments.

Glutamate secretion is taking place in cultured podocytes stimulated with 0.5 nM α-latrotoxin (continuous exocytosis) and 2.5 nM α-latrotoxin (burst of neurotransmitter release, followed by steady state).

Absence of glutamate release is observable when bafilomycin is added 30 min before the addition of latrotoxin (bafilomycin, 0.5M α-latrotoxin; bafilomycin, 2.5 nM α-latrotoxin) as well as in all negative controls (cells only, bafilomycin and cells, medium only, bafilomycin and medium).

Results are expressed as generation of NADH (Optical density at 340 nm, Y axis, mean values±standard deviation). On the X axis time points are indicated, ltx=latrotoxin addition. Bafilomycin was always added at −30'.

Panel b)-e): Rab3A (b, d) and glutamate (c, e) staining of cultured podocytes before (b, c) and after (d, e) nanomolar α-latrotoxin stimulus. Disappearance of most labeling from the processes of podocytes is evident after stimulation (indirect immunofluorescence, 450×).

Panel f): Inhibition curve (red line) obtained by coincubating 100 nM [$_3$H] with different concentrations (x axis) of cold L-glutamate (experiment performed in quadruplicate) in presence of Na+. The dotted black line indicates the results obtained by substituting cholineCl for Na+ in the assay buffer.

Figure 8:
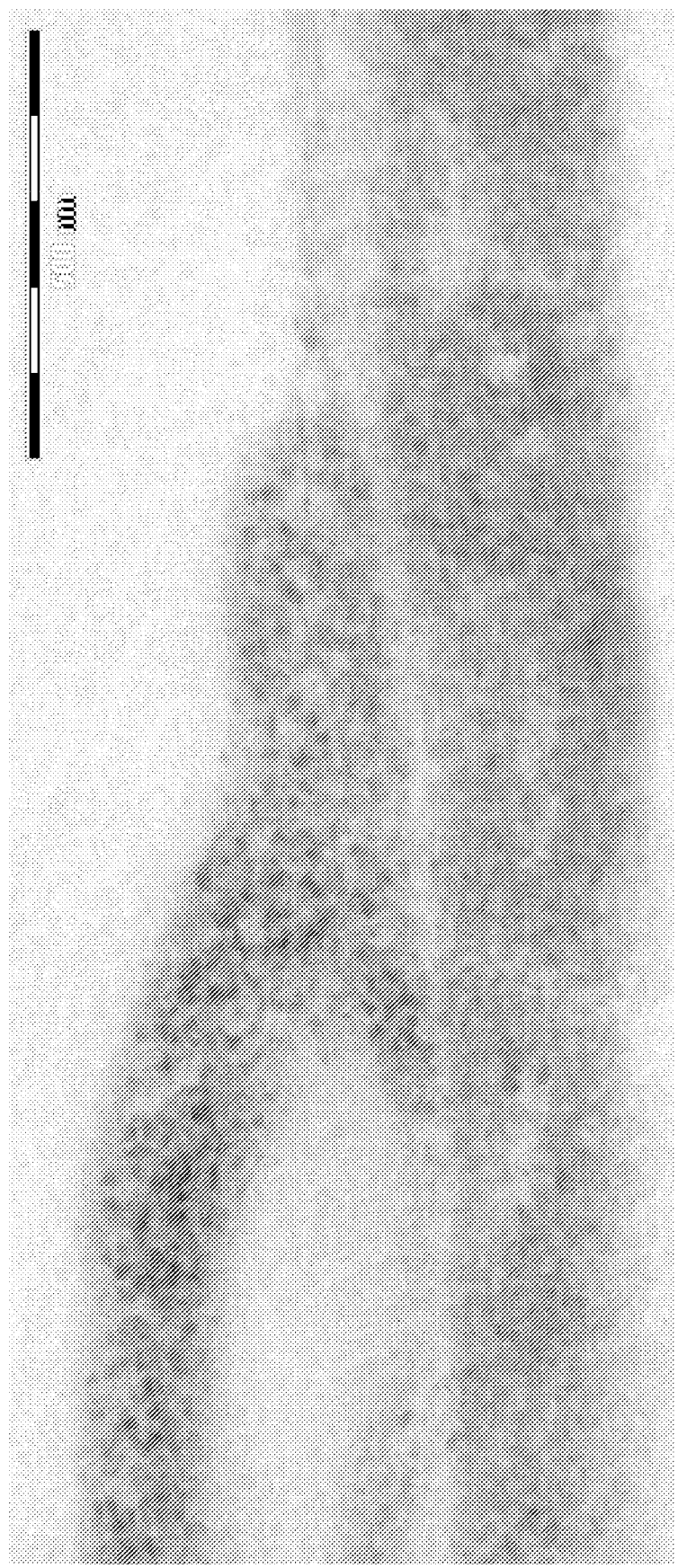

FIG. 8 Electon micrograph of a podocyte process bringing contact with another cell. Notice the morphologically striking similarity with synaptic contacts. (bar 500 nm).

Figure 9:
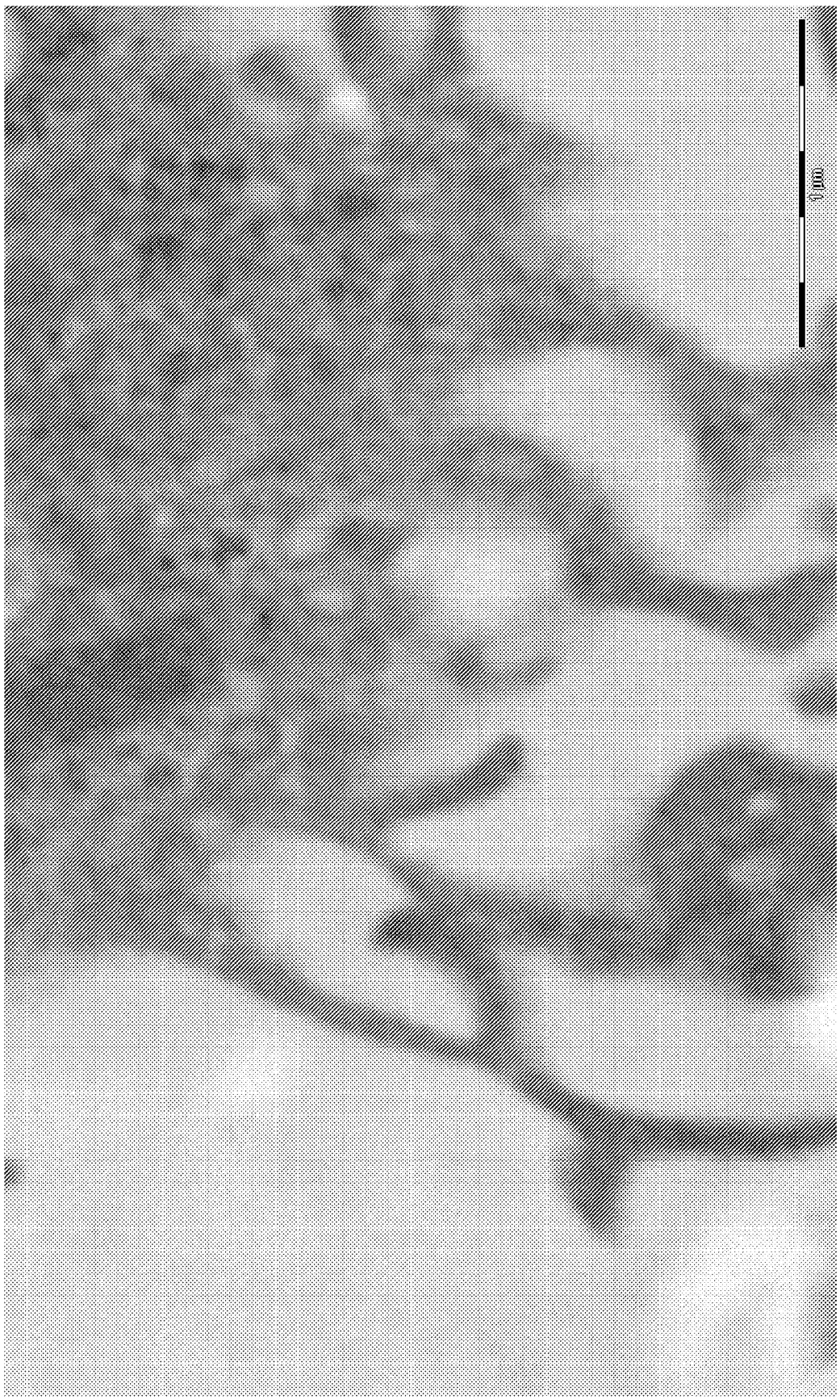

FIG. 9 Electron micrograph of a primary podocyte. A number of vesicles are present at the cell edge and along its processes. (bar 1 um).

Figure 10:

FIG. 10 Electron micrograph of a podocyte process forming junctions on both sides. Several vesicles are present in correspondence of the points of contact. (bar 500 nm)

Figure 11:
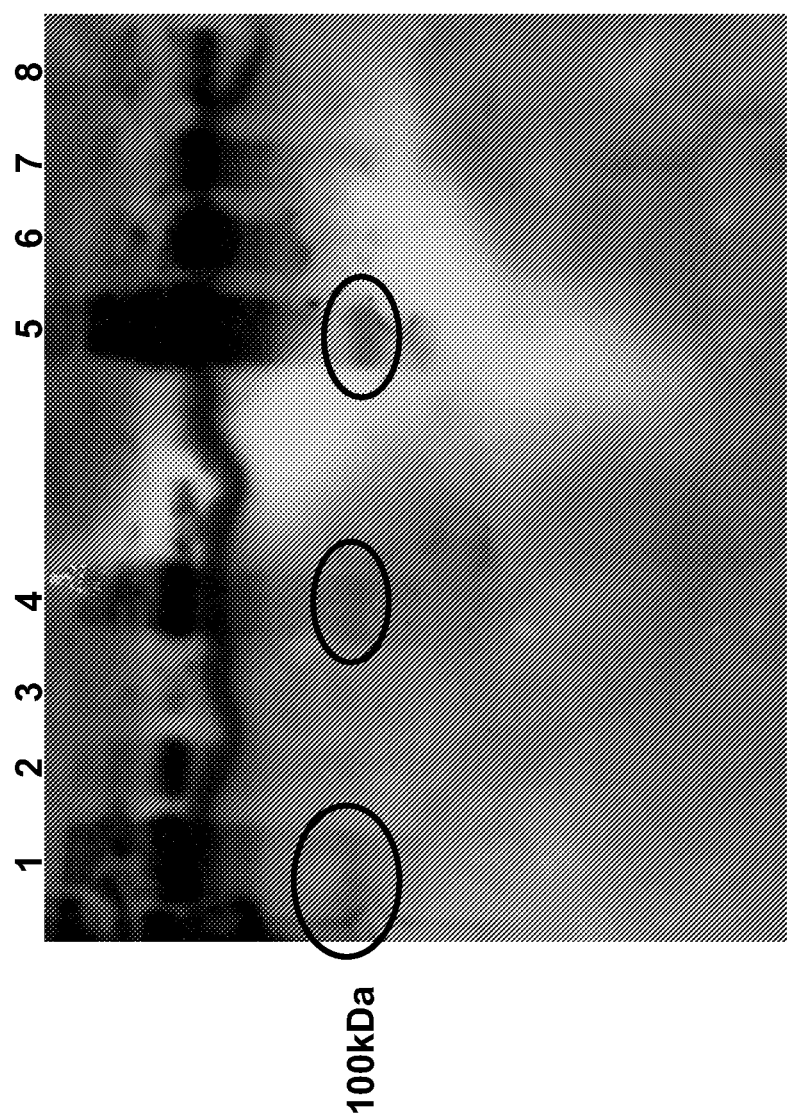

FIG. 11 Western blot analysis, performed on NMDA-1 receptor (line 1, line 4) and nephrin (line 5) immunoprecipitated from brain (line 1) and kidney glomeruli (line 4, line 5), using a rabbit anti-NMDA-1 receptor antibody, demonstrate specific bands of about 100 kDa. Lines 2, 6, 7: IgG controls; Lines 3, 8 negative controls.

Figure 12:
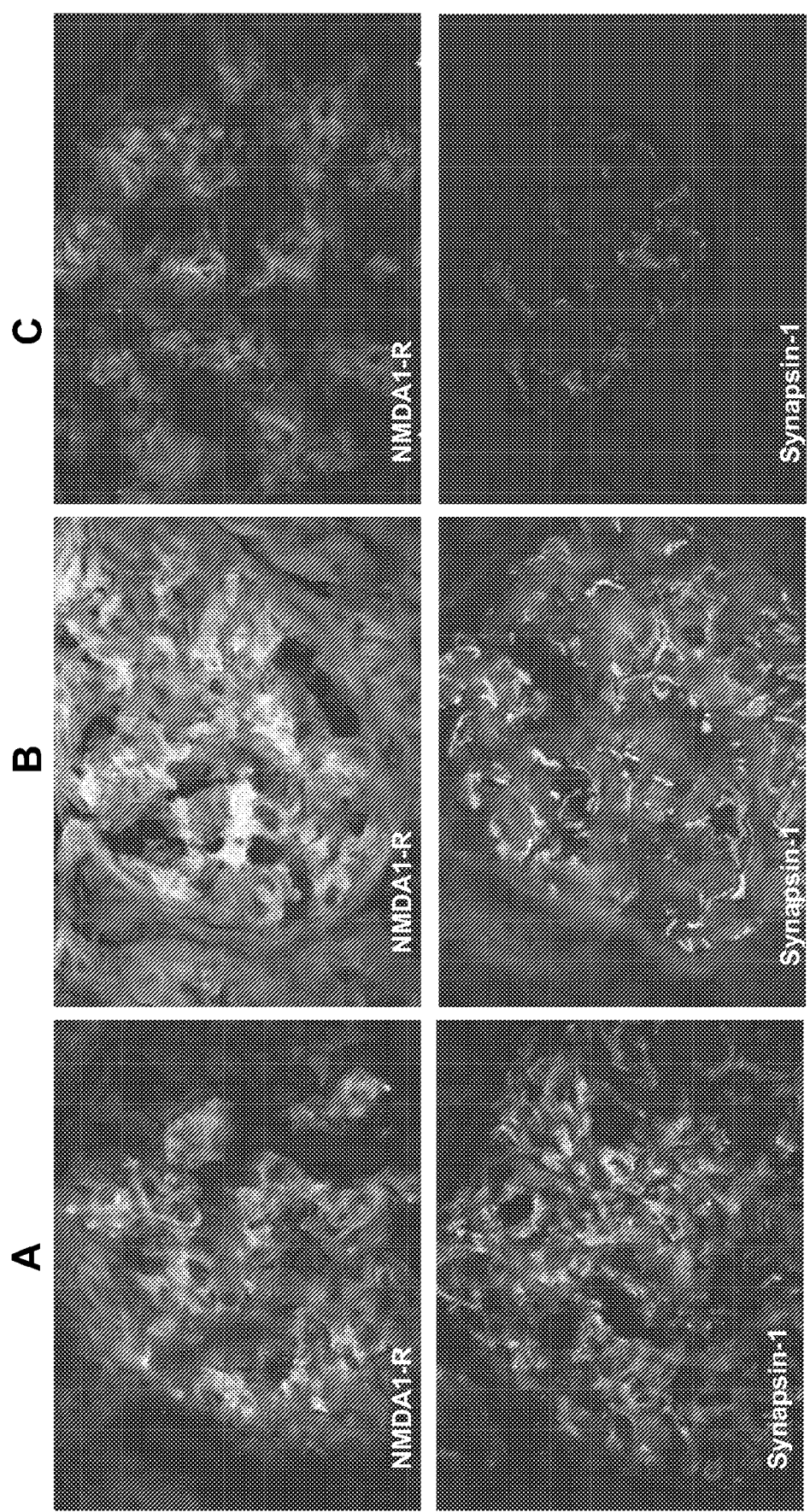

FIG. 12 Human glomeruli from patients with different types of glomerluonephriis show different patterns of expression of NMDA1 receptor and synapsin-1. The staining for both molecules can appear identical to normal kidney (column A, minimal change disease, membranous nephropathy), increased (column B, type II diabetic nephropathy, lupus nephritis) or almost completely negative (column C, IgA nephropathy, membranoproliferative glomerulonephritis). (Indirect immunofluorescence, 400×)

FIG. 13

A Phalloidin staining of primary mouse podocytes after 24 h medium incubation. The actin cytoskeleton is intact. Rhodamine-phalloidin, 100×)

B Phalloidin staining of primary mouse podocytes after 24 h 50 mM norketamine hydrochloride incubation. A profound alteration of the actin cytoskeleton is evident. (Rhodamine-phalloidin, 100×)

Figure 14:
Figure 14:
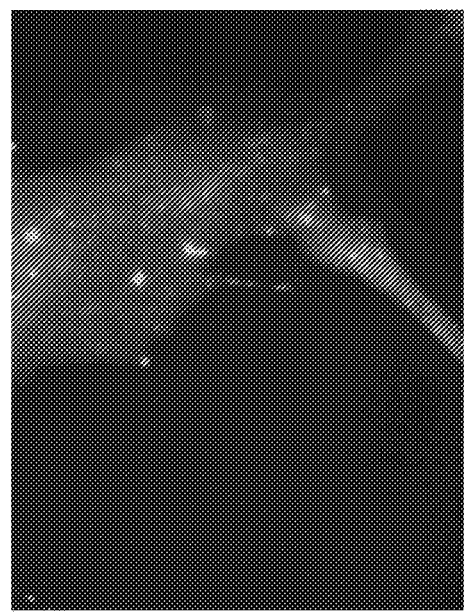
Figure 14:
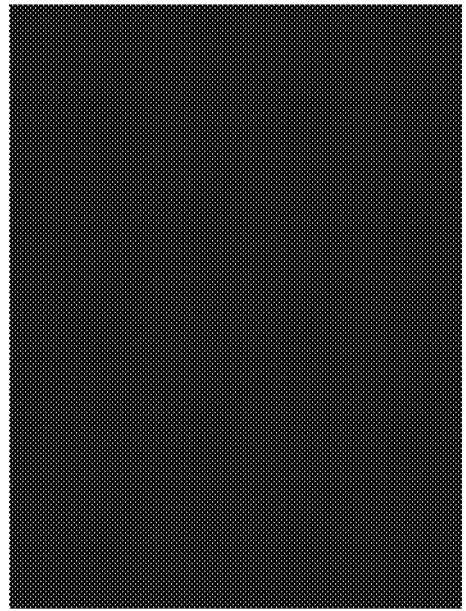
Figure 14:
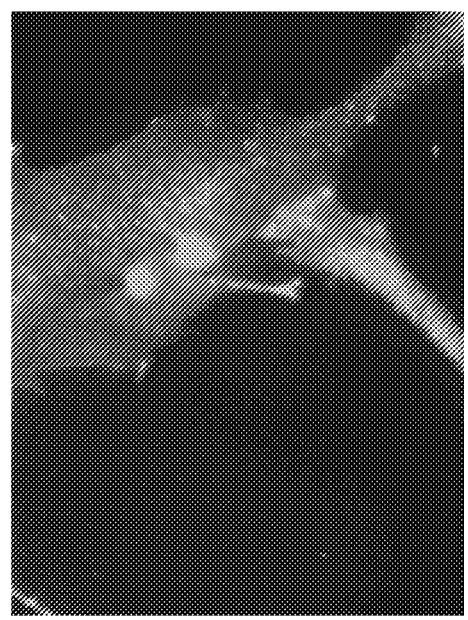
Figure 15:
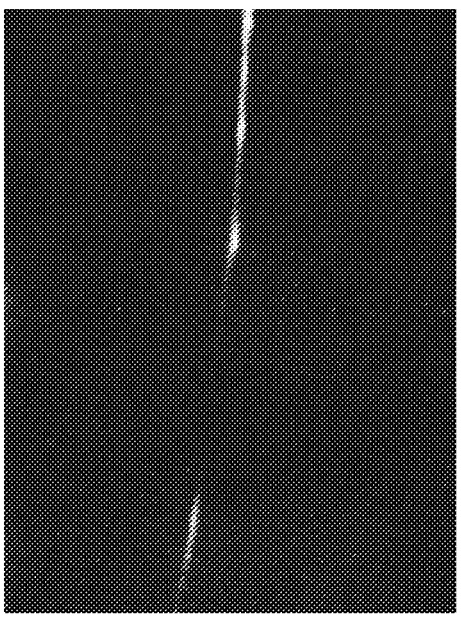
Figure 15:
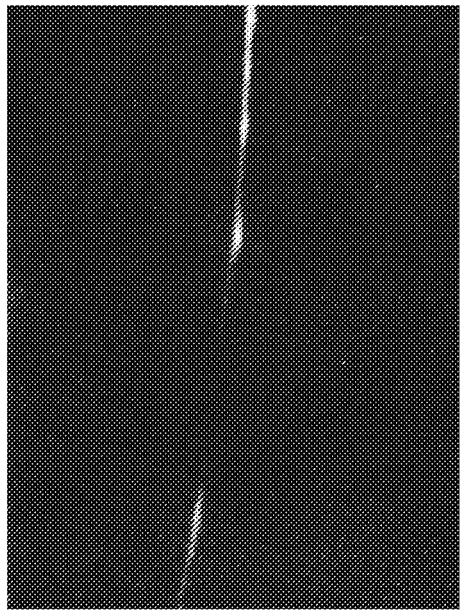
Figure 15:
Figure 15:
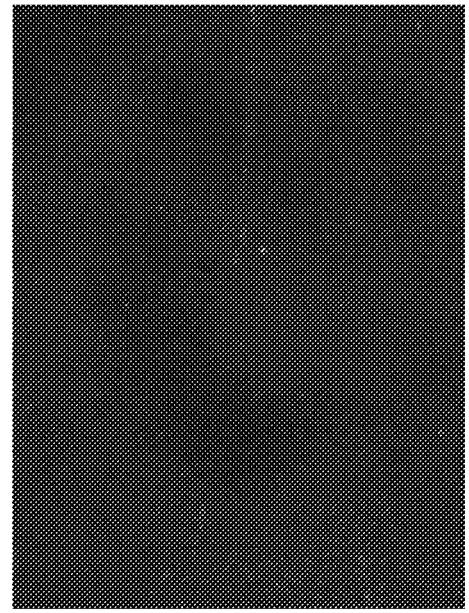
Figure 16:
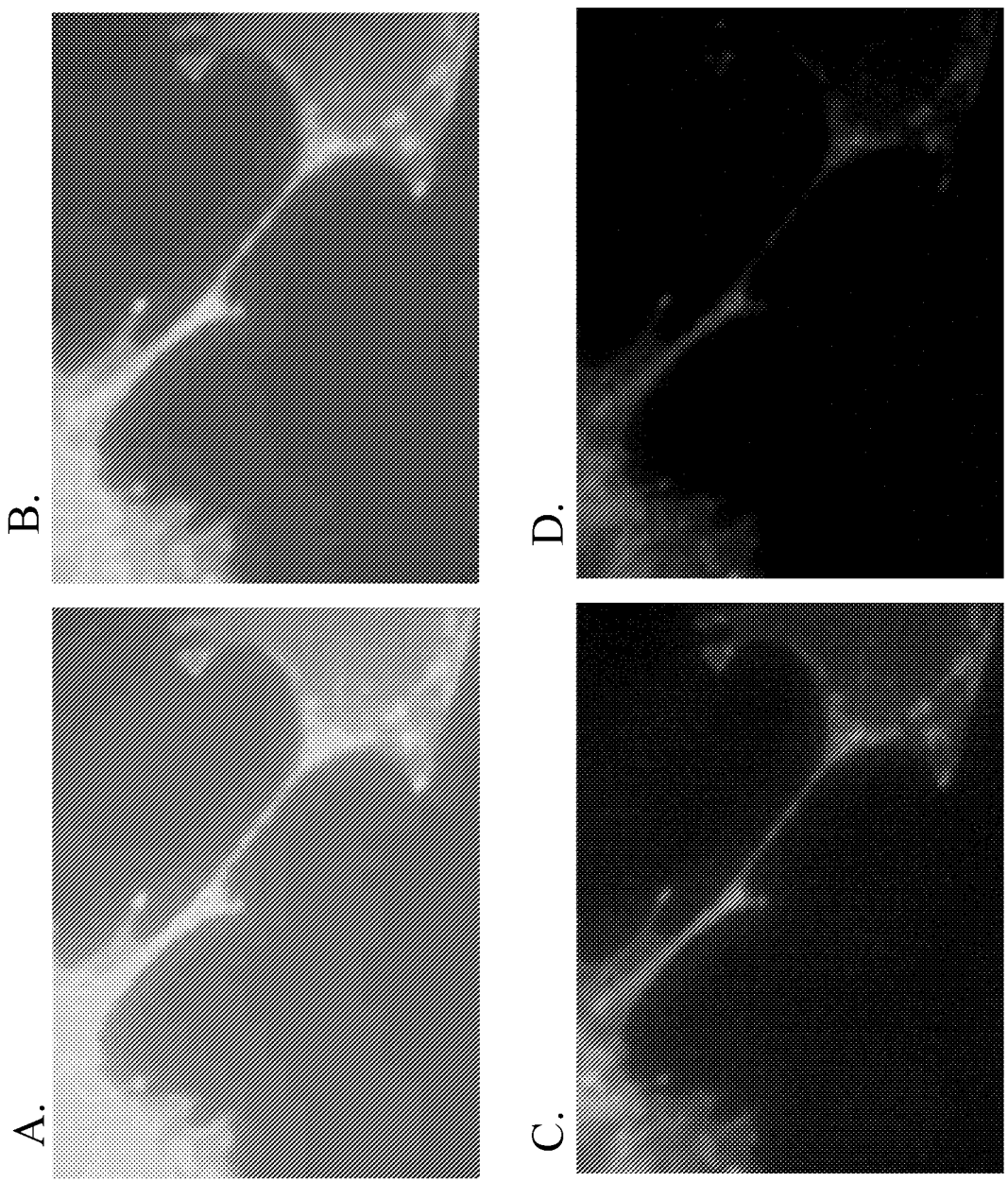
Figure 17:
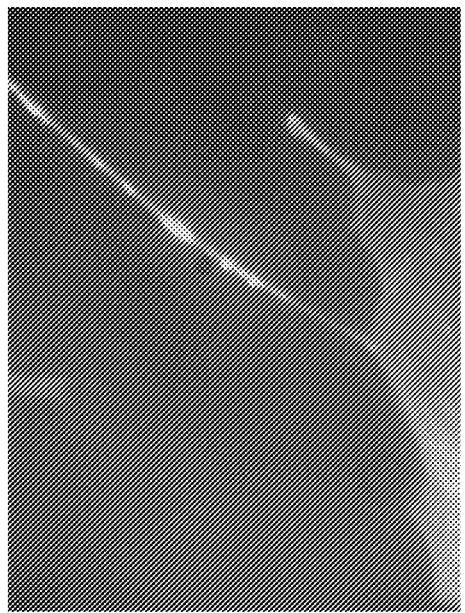
Figure 17:
Figure 17:
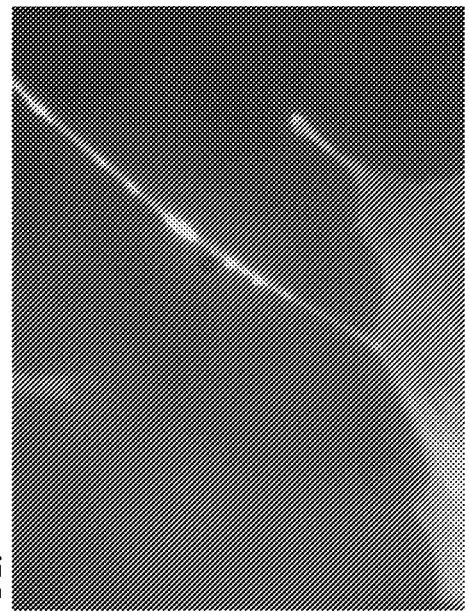
Figure 17:
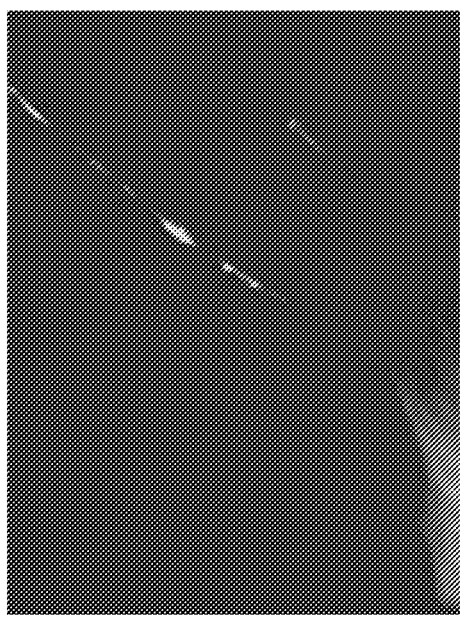

FIG. 14 Podocytes are incubated with 50 uM RH 414
A. a first image is taken after 15 min incubation
B. image taken after 15 sec
C. image taken after 45 sec
D. image taken after 60 sec FIG. 15 Podocotyes are incubated with 5 uM Fluo4
A. A first image is taken after 1 h incubation at 37° C.
B. Image taken after 1 sec 2 nM LTX
C. Image taken after 15 sec
D. Image taken after 30 sec FIG. 16 Podocytes are incubated with 5 uM Fluo4
A. A first image is taken after 1 h incubation at 37° C.
B. Image taken after 1 sec 2 nM LTX
C. Image taken after 15 sec
D. Image taken after 30 see FIG. 17 Podocytes are incubated with 1 uM Lysosensor Green DND-189
A. A first image taken after 5 min incubation
B. Image taken after 1 sec 2 nM LTX
C. Image taken after 45 sec
D. Image taken after 60 sec FIG. 18
A) Bright-field image (200×) showing the in vivo appearance of a primary podocyte before BDNF treatment.
B) The same field is taken after 20 h of BDNF incubation. The cell has produced a number of processes starting from its body.

Figure 19:
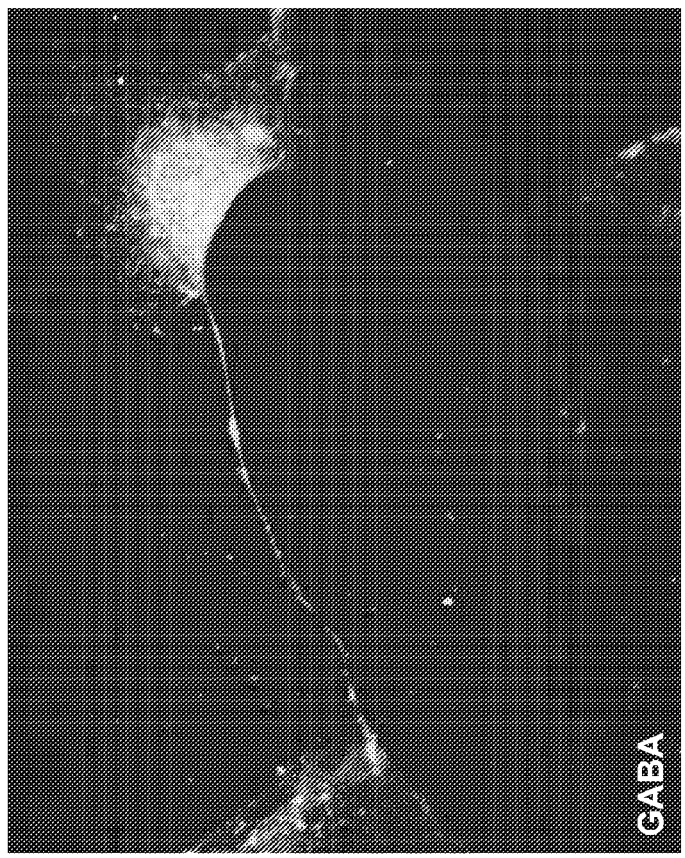
Figure 19:
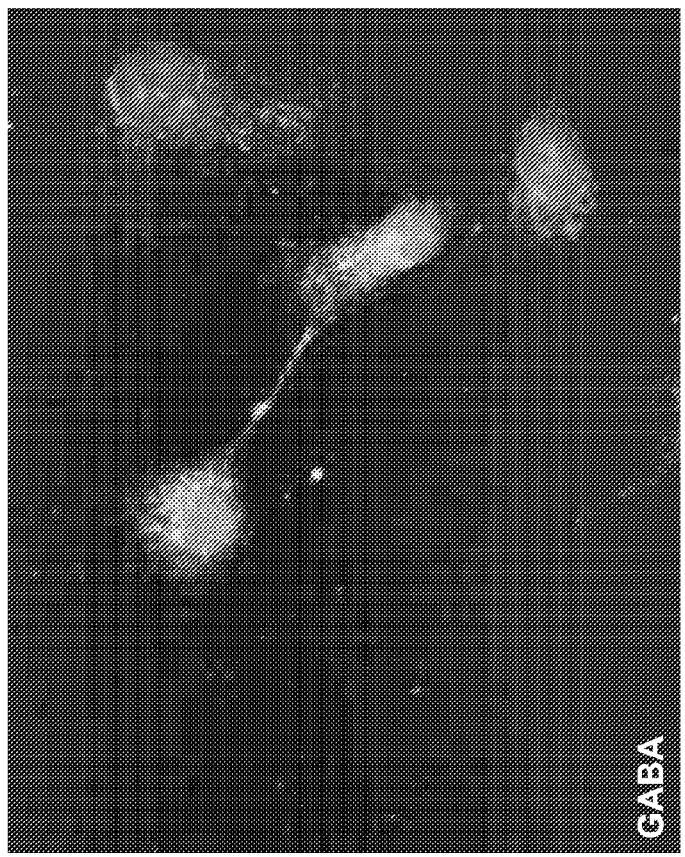

FIG. 19 GABA stains some cells in a primary podocyte cell culture (indirect immunofluorescence, 400×)

Figure 20:
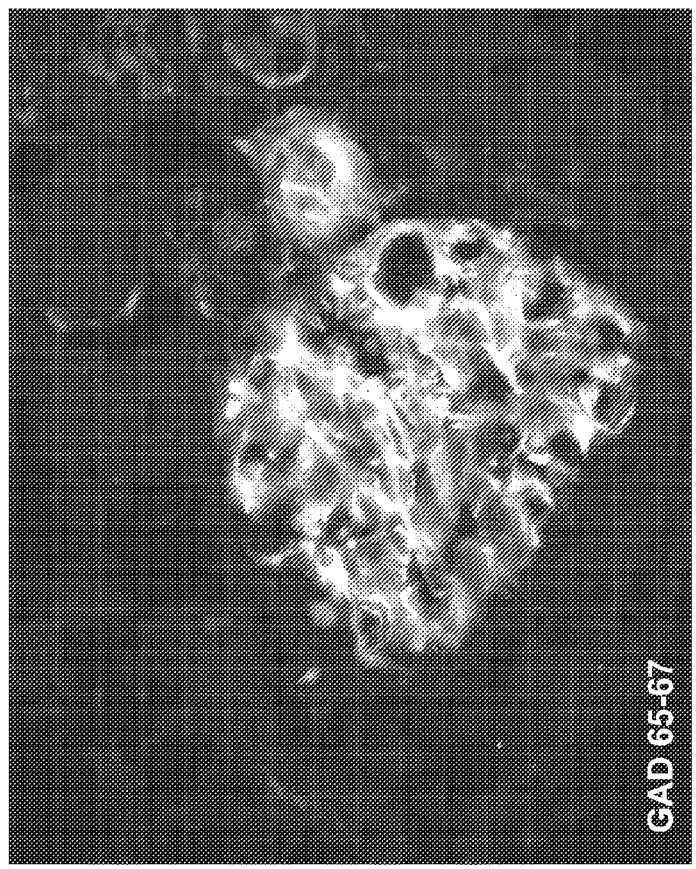
Figure 20:
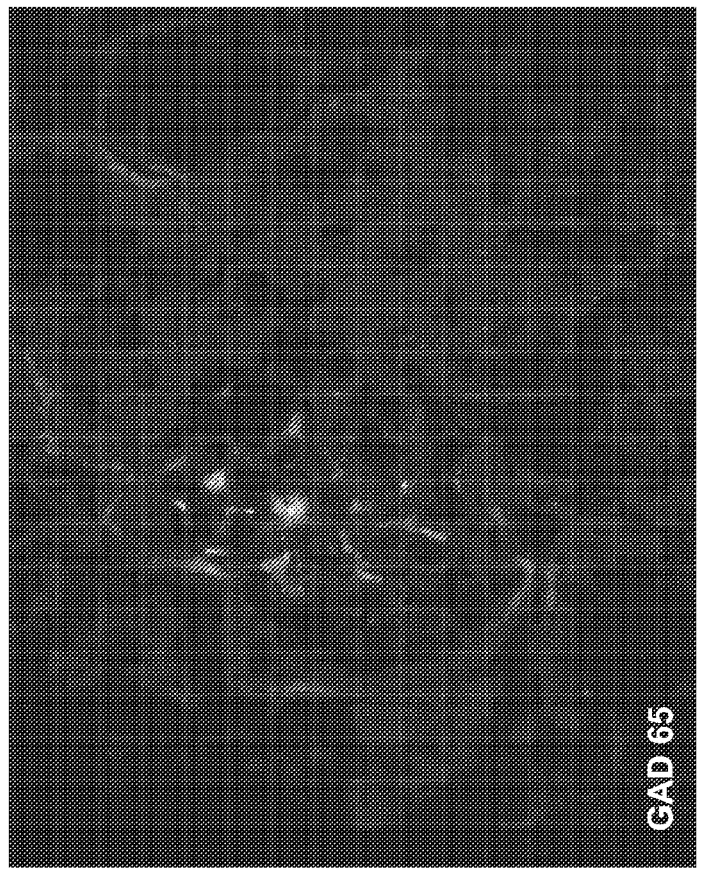

FIG. 20 GAD65 and GAD65-67 staining in normal mouse glomeruli. While GAD65 looks negative, a glomerular positivity for GAD65-67 is evident (indirect immunofluorescence, 400×)

Figure 21:
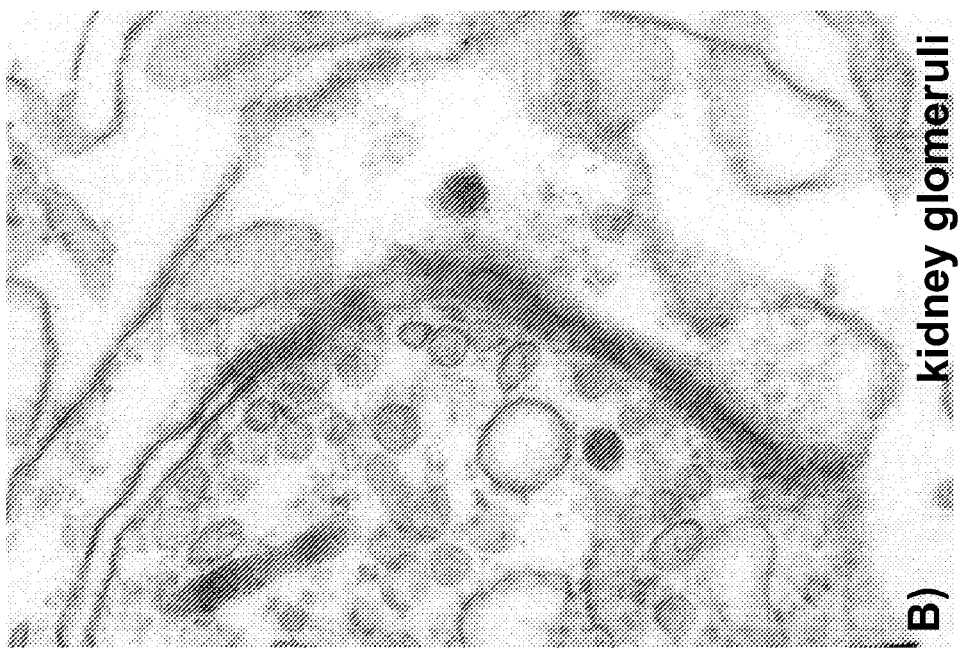
Figure 21:
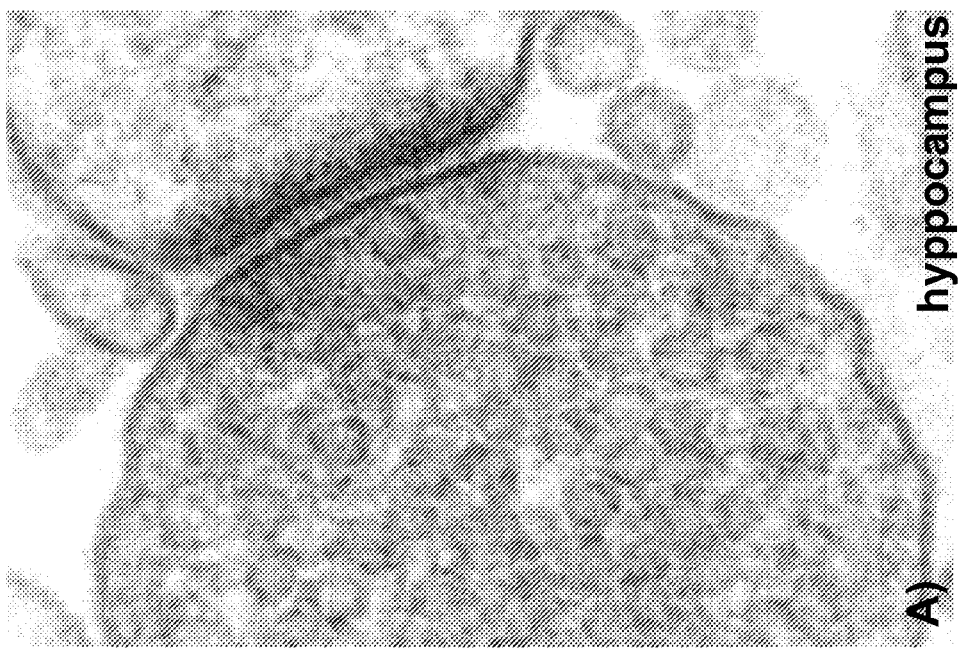
Figure 21:
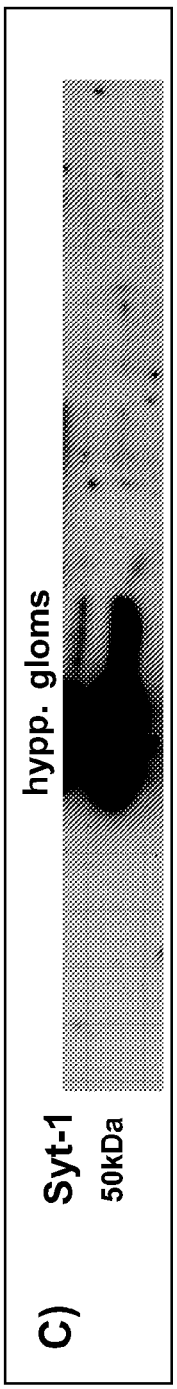

FIG. 21 Panel A): electron micrograph of a synaptosome separated from mouse hyppicampus.
Panel B): electron micrograph of a glomerular membrane-surrounded group of vesicular structures. The membrane maintains a junctional contact with another membrane.
Panel C): western blot Synaptotagmin 1 positivity of two separated fractions, one from glomerular extracts (gloms)

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). These documents are incorporated herein by reference.

"Expression" refers to the transcription of a genes DNA template to produce the corresponding mRNA and translation of this mRNA to produce the corresponding gene product (i.e., a peptide, polypeptide, or protein).

"Gene" is a segment of DNA that contains all the information for the regulated biosynthesis of an RNA product, including promoters, exons, introns, and other untranslated regions that control expression.

"Single Nucleotide Polymorphism (SNP)" refers to the specific pair of nucleotides observed at a single polymorphic site.

Rab3A

Rab proteins constitute the largest family of small GTPases that function as molecular switches and are generally involved in membrane traffic regulation in every cell. For this reason, most Rab proteins are ubiquitous, although vesicle specific. Based on their function and specific protein motifs, Rab proteins can be divided in several subgroups targeting specific subcellular compartments$_2$.

Rab3A belongs to the exocytic subgroup and, being involved in processes of highly regulated exocytosis, is restricted to few cellular elements3 and is most abundant in neurons, where it seems to modulate the vesicle fusion step at the presynaptic membrane$_4$. The Rab3A UniGene cluster is set out in Hs27744. The sequence for human Rab3A is set out in C34323 (GI:106186).

It has previously been observed that glomerular podocytes, highly differentiated cells with a crucial role in the glomerular filtration barrier, possess Rab3A, a GTPase restricted to cell types capable of highly regulated exocytosis.

The discovery that Rab3A is present in podocytes$_5$, crucial players in the maintenance of the glomerular filtration barrier, has raised the question of its function in these cells, where an activity of highly regulated exocytosis has never been discussed. However, podocytes possess Rab3A in addition to all other ubiquitously expressed Rab proteins$_6$ and the molecule is present around vesicles contained in the foot processes.

Methods for Detecting Rab3A Expression

Methods for detecting gene expression are well known to those skilled in the art and include, for example, immunohistochemistry and molecular probe analysis. Suitable methods are described herein. Suitable antibodies for immunohistochemistry are described herein. In one embodiment, antibodies which recognised a mutated form of Rab3A may be generated.

Methods for Identifying SNPs

A wide variety of assays for identifying and characterising SNPs in a sample are currently used. These include restriction fragment length polymorphism analysis (RFLP), single strand conformation polymorphism analysis (SSCP) (Orita et al. P.N.A.S. USA, 1989, 86: 2766-2770) allele specific oligonucleotide hybridisation (ASO) (Saiki et al. P.N.A.S. USA, 1989, 86:6230-6234) oligonucleotide ligation assay (OLA) (Landegren et al. 1988, Science 241; 1077-1080), ARMS (amplification refractory mutation system), primer extension or mini-sequencing type assays, Syvanen et al. 1999; Hum. Mutat. 13:1-10), TaqMan® (Livak et al. 1995; Nat. Genet. 9: 341-342), molecular beacons (Tyagi et al. 1998; Nat. Biotechnol. 16:49-53), nuclease (Goldrick 2001; Hum. Mutat. 18; 190-204) and structure-specific nuclease invader technology (Fors et al. 2000; Pharmacogenomics; 1:219-229)

The read out from these assays can be any of a number of types: radioactive, fluorescent, chemiluminescent, enzymatic, analysis of size, charge or mass etc.

A variety of technology platforms have been developed to increase throughput. A number of such platforms are reviewed, for example by Weiner and Hudson in BioTechniques 32; S4-S13 (June 2002).

Most assays and platforms for SNP and haplotype analysis start off with genomic DNA and require some form of amplification step.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification methods have been described in the literature, for example, general reviews of these methods in Landegren, U., et al., Science 242:229-237 (1988) and Lewis, R., Genetic Engineering News 10:1, 54-55 (1990).

PCR is a nucleic acid amplification method described inter alia in U.S. Pat. Nos. 4,683,195 and 4,683,202. PCR can be used to amplify any known nucleic acid in a diagnostic context (Mok et al., (1994), Gynaecologic Oncology, 52: 247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al. (1990) Proc. Natl. Acad. Sci. USA 87:1874). Ligation amplification reaction or ligation amplification system uses DNA ligase and four oligonucleotides, two per target strand. This technique is described by Wu, D. Y. and Wallace, R. B. (1989) Genomics 4:560. In the Q β Replicase technique, RNA replicase for the bacteriophage Q β, which replicates single-stranded RNA, is used to amplify the target DNA, as described by Lizardi et al. (1988) Bio/Technology 6:1197.

Alternative amplification technology can be exploited in the present invention. For example, rolling circle amplification (Lizardi et al., (1998) Nat Genet 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., (1992) PNAS (USA) 80:392) begins with a specifically defined sequence unique to a specific target.

Primers suitable for use in various amplification techniques can be prepared according to methods known in the art.

Compositions for detecting Rab3A SNPs can comprise at least one Rab3A genotyping oligonucleotide. Suitably, a Rab3A genotyping oligonucleotide is a probe or primer capable of hybridizing to a target region that is located close to, or that contains, the polymorphic sites described herein.

As used herein, the term "oligonucleotide" refers to a polynucleotide molecule having less than about 100 nucleotides. Suitably, an oligonucleotide of the invention is 10 to 35 nucleotides long. More preferably, the oligonucleotide is between 15 and 30, and most preferably, between 20 and 25 nucleotides in length. The oligonucleotide may be comprised of any phosphorylation state of ribonucleotides, deoxyribonucleotides, and acyclic nucleotide derivatives, and other functionally equivalent derivatives. Alternatively, oligonucleotides may have a phosphate-free backbone, which may be comprised of linkages such as carboxymethyl, acetamidate, carbamate, polyamide (peptide nucleic acid (PNA)) and the like (Varma, R. in Molecular Biology and Biotechnology, A Comprehensive Desk Reference, Ed. R. Meyers, VCH Publishers, Inc. (1995), pages 617-620).

Oligonucleotides may be prepared by chemical synthesis using any suitable methodology known in the art, or may be derived from a biological sample, for example, by restriction digestion. The oligonucleotides may be labeled, according to any technique known in the art, including use of radiolabels, fluorescent labels, enzymatic labels, proteins, haptens, antibodies, sequence tags and the like.

Genotyping probes or oligonucleotides of use in the methods of the present invention must be capable of specifically hybridizing to the target region of a Rab3A polynucleotide in which the polymorphisms are located. As used herein, specific hybridization means the oligonucleotide forms an antiparallel double-stranded structure with the target region under certain hybridizing conditions, while failing to form such a structure when incubated with a non-target region or a non-Rab3A polynucleotide under the same hybridizing conditions. Preferably, the oligonucleotide specifically hybridizes to the target region under conventional high stringency conditions. The skilled artisan can readily design and test oligonucleotide probes and primers suitable for detecting polymorphisms in the Rab3A gene using the polymorphism information provided herein in conjunction with the known sequence information for the Rab3A gene and routine techniques.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions.

Conventional hybridization conditions are described, for example, by Sambrook J. et al., in Molecular Cloning, A Laboratory Manual, $2^{nd}$ Edition, Cold Spring Harbor Press, Cold Spring Harbor, N.Y. (1989) and by Haymes, B. D. et al. in Nucleic Acid Hybridization, A Practical Approach, IRL Press, Washington, D.C. (1985). While perfectly complementary oligonucleotides are preferred for detecting polymorphisms, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the oligonucleotide probe or primer as long as the resulting probe or primer is still capable of specifically hybridizing to the target region.

Typically, the nucleic acid mixture is isolated from a biological sample taken from the individual, such as a blood sample or tissue sample. Suitable tissue samples include whole blood, semen, saliva, tears, urine, fecal material, sweat, buccal, skin and hair. The nucleic acid mixture may be comprised of genomic DNA, mRNA, or cDNA and, in the latter two cases, the biological sample must be obtained from an organ in which the Rab3A gene is expressed. Furthermore it will be understood by the skilled artisan that mRNA or cDNA preparations would not be used to detect polymorphisms located in introns or in 5' and 3' nontranscribed regions. If a Rab3A gene fragment is isolated, it must contain the polymorphic site(s) to be genotyped.

Thus, the invention also provides a diagnostic kit for diagnosing a nephropathy comprising a set of genotyping oligonucleotides for genotyping Rab3A Diseases As indicated above, the present invention may be employed to treat, diagnose, or help predict the onset of a number of nephropathies.

In aspects of the invention involving treatment, we include any therapeutic application that can benefit a human or non-human animal. The treatment of mammals is particularly preferred. Both human and veterinary treatments are within the scope of this invention. Treatment may be in respect of an existing condition or it may be prophylactic.

In one embodiment, a defective Rab3A gene or expression may be corrected by administration of a non-mutated Rab3A gene to a patient suffering from a relevant disease or condition. Administration can be in a number of ways. The delivery system of the present invention may be a viral or non-viral delivery system. Non-viral delivery mechanisms include but are not limited to lipid mediated transfection, liposomes, immunoliposomes, lipofectin, cationic facial amphiphiles (CFAs) and combinations thereof. As previously indicated when the agent is delivered in the form of a polynucleotide to a cell for subsequent expression therein the agent is preferably delivered via a retroviral vector delivery system. However, the polynucleotide may be delivered to the target cell population by any suitable Gene Delivery Vehicle, GDV. This includes but is not restricted to, DNA, formulated in lipid or protein complexes or administered as naked DNA via injection or biolistic delivery, and viruses such as retroviruses. Alternatively, the polynucleotides are delivered by cells such as monocytes, macrophages, lymphocytes or hematopoietic stem cells. In addition, a cell-dependent delivery system may be used. In this system the polynucleotides encoding the agent are introduced into one or more cells ex vivo and then introduced into the patient.

The agents of the present invention may be administered alone but will generally be administered as a pharmaceutical composition.

Pharmaceutical Compositions

The present invention thus also extends to pharmaceutical compositions. A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Suitably a pharmaceutical composition or a medicament in accordance with the comprises a modulator of a synapse-specific protein.

"Therapeutically effective amount" refers to the amount of the therapeutic agent which is effective to achieve its intended purpose. While individual patient needs may vary, determination of optimal ranges for effective amounts of Rab3A is within the skill of the art. Generally the dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination and can be adjusted by one skilled in the art. Thus, the dosage regimen actually employed may vary widely and therefore may deviate from the preferred dosage regimen set forth herein.

The invention is further described, for the purposes of illustration only, in the following examples.

EXAMPLES

Example 1

Methods

Animal Model

All mouse protocols were approved by the Milan University Institutional Care and Ethical Treatment Committee. Rab3A knock-out mice (KO, Rab3a−/−, $Rab3a_{tm1Sud}$) and their wild-type counterpart (WT, Rab3A+/+) in B6 background (B6129SF2/J) were bought from the Jackson Laboratory (Bar Harbor, Me., USA), housed on a 12-h light/dark cycle, and allowed free access to food and water.

From any newborn, a tail sample was used to verify the genotype, according to the PCR scheme specifically designed (http://www.jax.org), given that in the knock-out the promoter and the first two exons of the RAB3A gene have been replaced by a neomycin cassette. 24 hours urine collection was obtained monthly in metabolic cages, to assess albumin (ELISA test, Bethyl Laboratories) and creatinine (Sentinel Kit, Sentinel, Milan, Italy) values.

Groups of animals were sacrificed at the age of 1 week, 1, 3, 6, and 9 months, and the organs taken for histological, immunohistological and electron microscopy procedures.

Human Material

All human material, collected in a European multicenter study, the European cDNA Bank (ERCB), and in a Chinese Nephrology Unit, was obtained after informed consent of the patients and with acknowledgment of the local ethical committees. Kidney biopsy samples were taken from subjects affected by proteinuric conditions for diagnostic purposes. Normal kidneys were from the unaffected pole of tumor nephrectomies and from pre-transplantation kidney biopsies from living and cadaveric donors. Blood samples were obtained from nephropathic patients and voluntary control subjects.

Podocyte Cell Cultures

Kidneys taken from 2-4 week old normal mice were decapsulated, washed in Ca++ and Mg++ free Hanks medium and treated with collagenase type I AS (Sigma-Aldrich) 1.5 mg/ml, for 1 min at 37° C. The reaction was stopped by growth medium consisting of DMEM:F12 supplemented with 10% FCS, 5 µg/ml Transferrin, $10_{-7}$M Hydrocortisone, 5 ng/ml Sodium Selenite, 0.12 U/ml Insulin, 100 µg/ml Penicillin, 100 µg/ml Streptomycin, 2 mM L-Glutamine (Sigma-Aldrich).

Glomeruli were isolated by sieving, as described by Mundel et al[43], further manually purified, then seeded in culture flasks (Corning) precoated with collagen type IV (Sigma-Aldrich) at 37° C. in 5% $CO_2$ atmosphere. On days 4 to 5 podocyte growth started and allowed by day 8 to detach glomeruli using trypsin-EDTA.

First passage podocytes, which resulted in >95% pure as judged by light microscopy inspection, were seeded on flasks and chamber slides. Cell characterization was performed by immunohistochemistry, using podocyte (nephrin, synaptopodin, WT1), epithelial (cytokeratins), smooth muscle (alpha-smooth muscle actin) and endothelial cell (CD31) markers.

α-Latrotoxin Assay

α-Latrotoxin stimulated glutamate release was detected by an enzymatic assay based on the following reaction that occurs in presence of glutamate dehydrogenase (GDH): $Glutamate_- + NAD_+ + H_2O \rightarrow ketoglutarate_2 + NADH + NAD_{4+} + H_+$.

Briefly, to this purpose, the same numbers of podocytes obtained from normal mouse glomeruli were plated and grown to semiconfluence. Before measurements, cells were washed and re-suspended for 1 hour at 37° C. in DME incubation buffer (NaCl 109.5 mM, KCl 5.3 mM, glucose 5.5 mM with $MgCl_2$ 1 mM, Hepes 20 mM). The medium was further supplemented with GDH (Sigma 60 U/ml) and NAD+ (Sigma 1 mM), and incubated for 5 min. Then, α-latrotoxin was added at subnanomolar (0.5 nM) or nanomolar (2.5 nM) concentration and spectrophotometric increase of optical density (O.D.) due to increase of NADH was monitored at 340 nm. 200 nM Bafilomycin A1 (Sigma), a V-ATPase inhibitor that dissipates the electrochemical proton gradient necessary for glutamate uptake and storage into vescicles$_{43}$, was added for 30 min at 37° C. to control cell plates before α-latrotoxin stimulation.

[$_3$H]-L-Glutamate Uptake

Podocytes were seeded at a density of 15,000 cells/well in 48-well plates, Two days later the culture medium was removed, the adherent washed two times with 0.5 mL/well of assay buffer (10 mM Tris-acetate, 128 mM NaCl, 10 mM D-glucose, 5 mM KCl, 1.5 mM NaH$_2$PO$_4$, 1 mM MgSO$_4$, 1 mM CaCl$_2$, pH 7.4) and then incubated for 15 min at 35° C. in assay buffer (0.3 mL/well) containing 100 nM [3H]-L-glutamate (Amersham, specific activity 47.0 Ci/mmol) with or without different concentrations of cold L-glutamate (from 1 to 1000 µM). Non-specific uptake was determined in parallel samples incubated in a Na+-free buffer (NaCl replaced by cholineCl). Uptake was stopped by removing the incubation buffer and washing the cells two times with 0.5 mL/well of ice-chilled assay buffer.

In preliminary experiments it was established that the uptake of [$_3$H]-Lglutamate was linear at least up to 15 min (not shown). Cells were then added with 0.3 mL/well of SDS and, after 2 hours on shaking plate, the well content was counted in 4 mL of Ultima Gold MV (Packard Bioscience, Groningen, the Netherlands) in an LKB 1214 Rackbeta liquid scintillation counter with a counting efficiency of about 60%.

Km and Vmax of L-glutamate uptake were determined by fitting the inhibition curve using the "homologous competitive binding curve" equation built into GrapPad Prism version 4.00 for Windows (GraphPad Software, San Diego Calif. USA). 14

Immunoprecipitation

Glomeruli from normal mouse kidneys were isolated by sieving, as described by Mundel et al (1) and further purified manually under a stereomicroscope.

Protein extracts were prepared from isolated glomeruli and from normal mouse total brain by sonication in modified Ripa Buffer (10 mM TrisHCl pH 7.5, 110 mM EDTA, 0.5% NP-40, 0.5% DOC, 0.1% SDS) with addition of Protease inhibitor-cocktail (Roche).

Before immunoprecipitation, 400 µg of each lysate were precleared with protein G immobilized on agarose (Sigma) in 500 µl IP buffer (1% Triton X-100, 75 mM NaCl, 50 mM, Hepes pH 7.4, 1 mM EGTA, 1 mM Na$_3$VO$_4$, protease inhibitor) for 1 hour at 4° C. to remove proteins that may nonspecifically bind to the beads. Precleared lysates were immunoprecipitated for 2 hours at 4° C. with 5 µg of rabbit polyclonal anti-Rab3A antibody (Abcam) which had been first conjugated with protein C beads. The immunoprecipitates were pelleted by centrifuging 13.000 rpm for 10 min. at 4° C. and washed three times with IP buffer. A specificity-control with rabbit IgG (Zymed) and a negative control without antibody were added for each assay to test specificity of immunoprecipitation. Western Blot with a mouse monoclonal anti-Rab3A antibody (Synaptic System) in non reducing condition was performed to confirm the accuracy of immunoprecipitation.

Sample Preparation for MALDI-TOF-MS Analysis

Immunoprecipitated samples were separated by 10% sodium dodecyl polyacrylamide gels (SDS-PAGE) and silver-stained according to O'Connel and Stults (2). Six stained protein bands with approximate sizes ranging from of 30 to 100 kD were excised and cut into pieces. The stain was removed with 15 mM potassium ferricyanide in 50 mM sodium thiosulfate followed by washes with water, shrinking with acetonitrile (CAN), and drying in a vacuum centrifuge. Proteins were reduced with 20 mM dithiothreitol in 0.1 mM NH4HCO3 for 15 minutes at room temperature and water with ACN shrinking in between, followed by final CAN shrinking and drying in vacuum. In-gel trypsin digestion was performed with 0.05 µg/µl sequencing-grade modified trypsin (Promega, Madison, Wis.) in 10 mM NH4CO3/10% ACN on an ice bath for 10 minutes, followed by overnight incubation at 37° C. The digested peptides were extracted with 0.1/TFA/60% ACN and desalted by reverse phase material (ZIP TIP C18, Millipore, Bedford, Mass.) packed into a gel loading pipette tip according to manufacturer's instructions.

MALDI-TOF-MS Analysis

Fingerprinting for extracted peptides was performed with a Biflex matrix-assisted laser desorption/ionization-time of flight (MALDI-TOF) mass spectrometry (2 GHZ digitizer; Bruker, Rheinstetten, Germany) at a local protein chemistry unit (Biomedicum Helsinki). Positive ion reflector mode was used with an accelerating voltage of 19,000 V and delayed extraction of 2 ns. Internal peptide calibration standards (Bruker Daltons, Bremen, Germany) were applied to obtain higher peptide mass accuracy. Results were analyzed by Profound search engine (http://prowl.rockefeller.edu/profound_bin/WebProFound.exe).

Results

We have examined the hypothesis that in podocytes Rab3A may be involved in a secretory activity, which could serve as a tightly regulated mean of communication instrumental to neighbouring podocytes, mesangial and endothelial cells.

Rab3A Null Mice

First we have studied the effect of the lack of Rab3A in the kidney. Rab3A null mice were created and extensively studied from the neurological side by the group of T. Südhof[7, 8]. The authors described a phenotype characterized by abnormal regulation of synaptic vesicle exocytosis, with long-term potentiation impairment at hippocampal mossy fibre synapses.

Figure 1A:
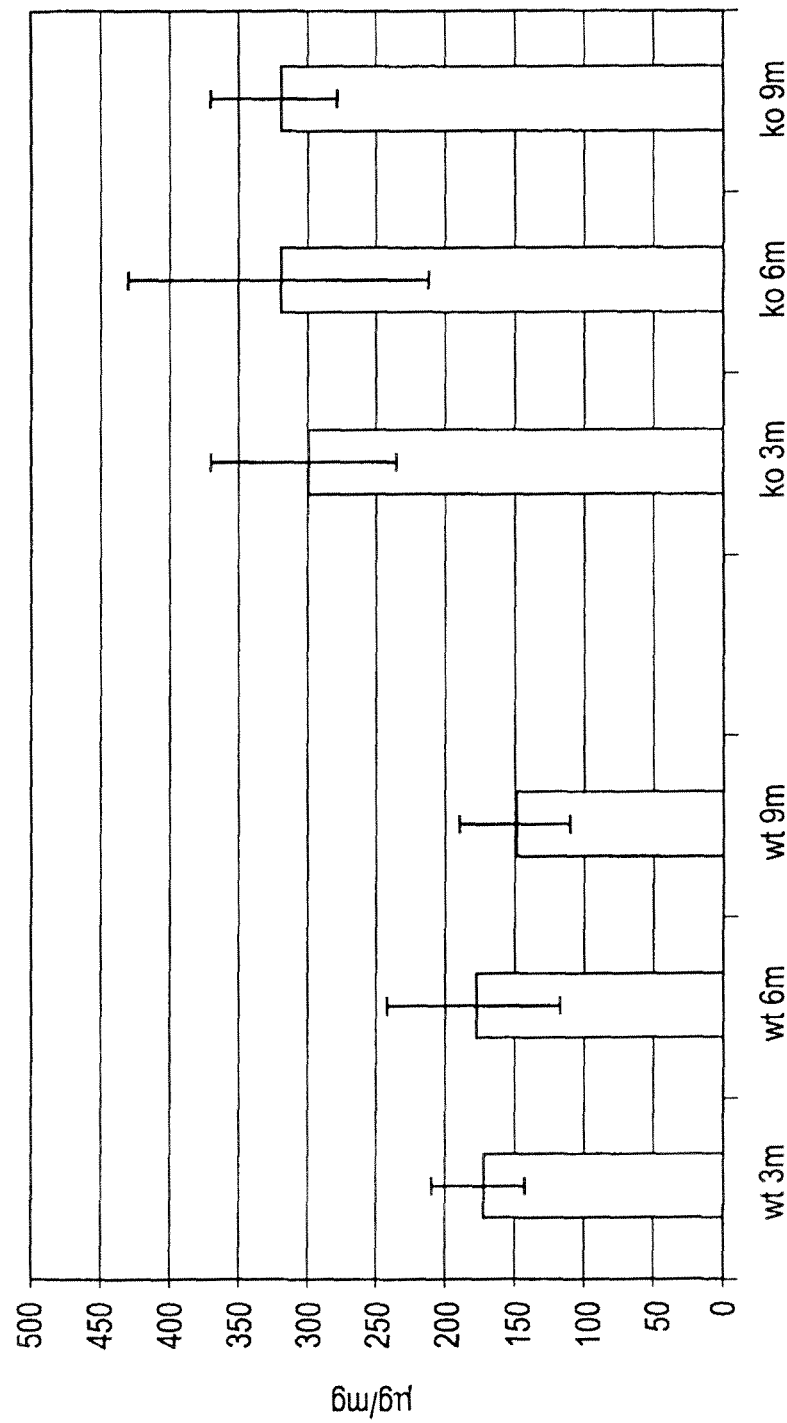
Figure 1B:
Figure 1D:
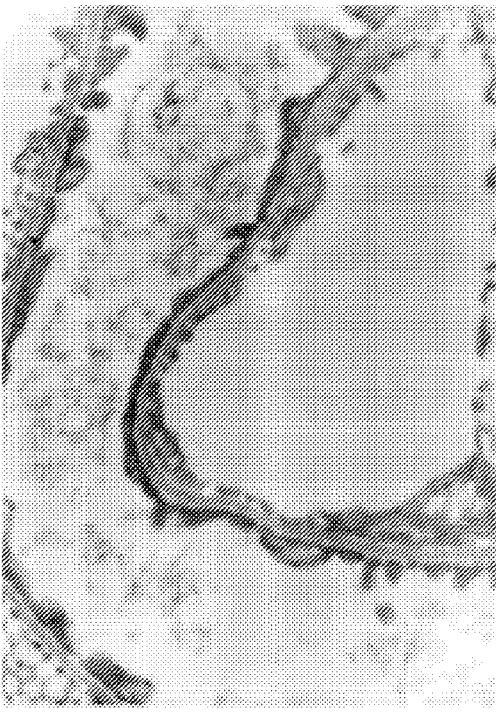
Figure 1C:
Figure 1E:
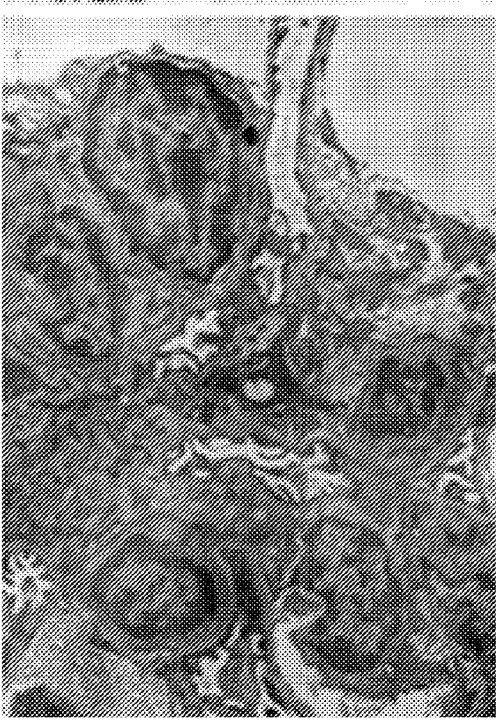
Figure 1F:
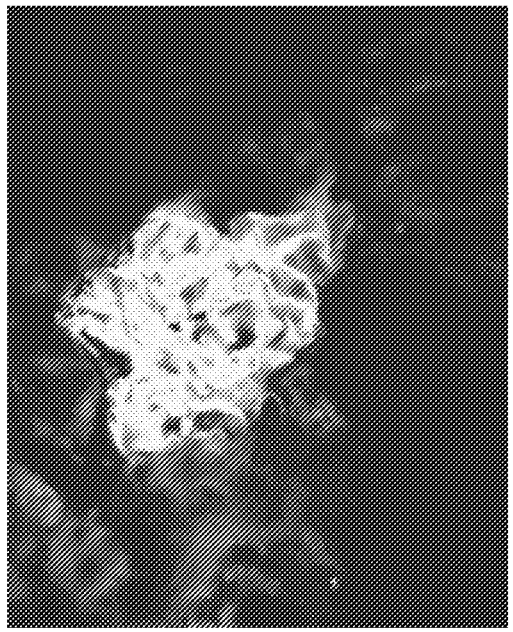
Figure 1G:
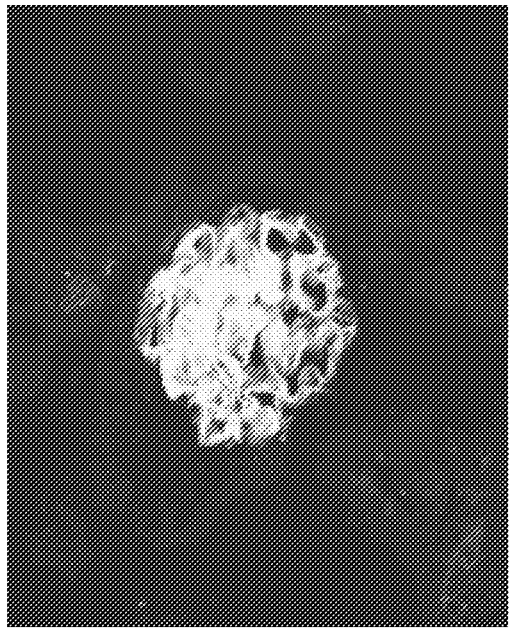
Figure 1H:
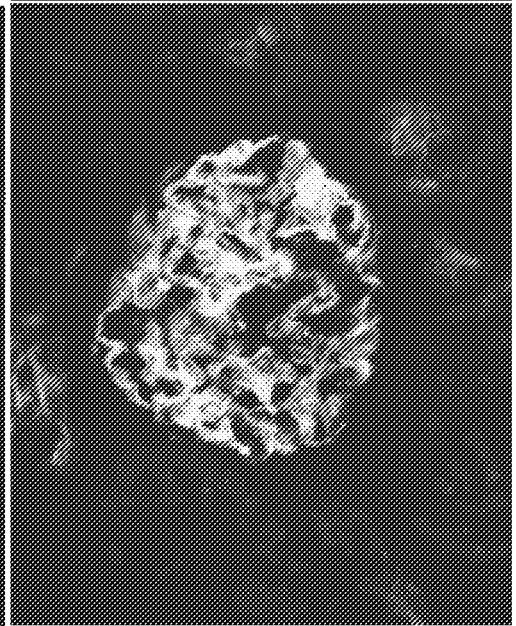
Figure 1I:
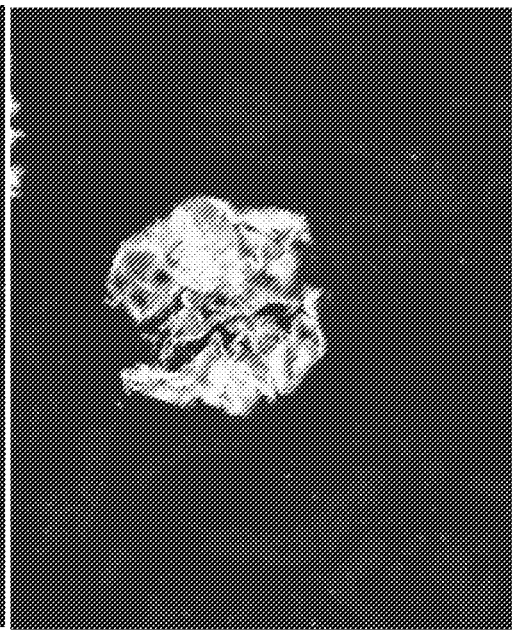
Figure 1K:
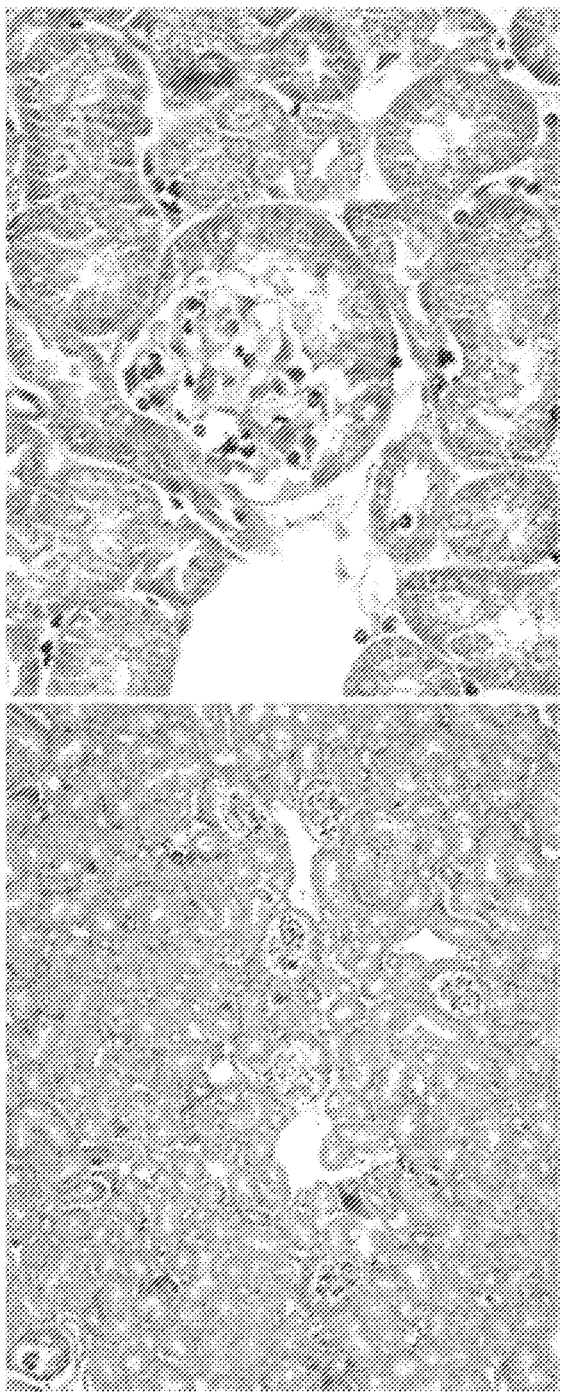
Figure 1M:
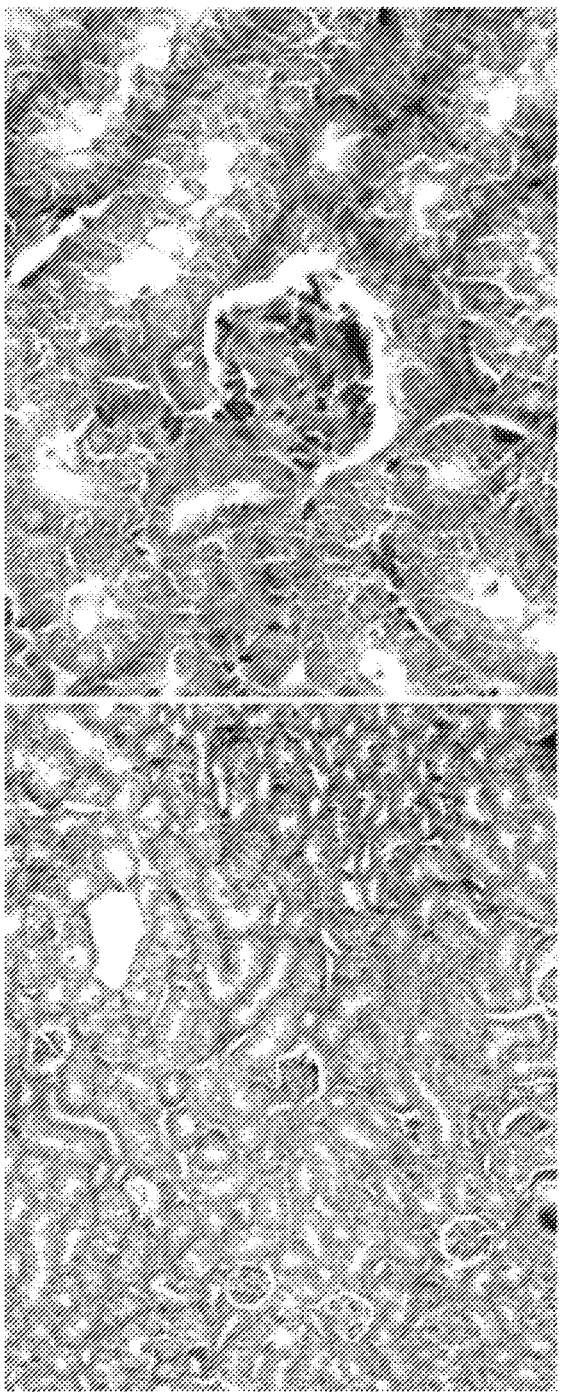
Figure 1J:
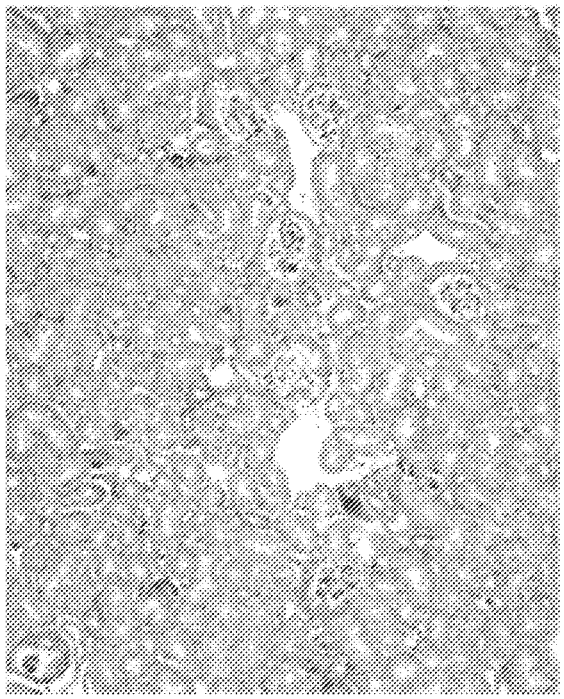
Figure 1L:
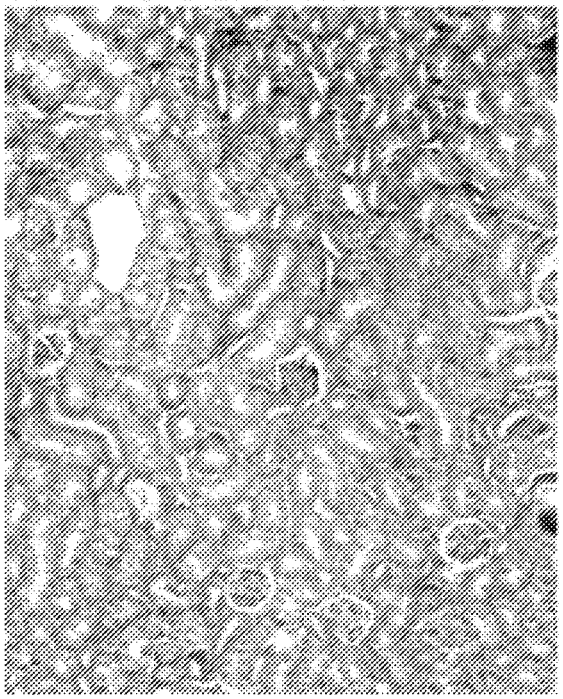
Figure 1O:
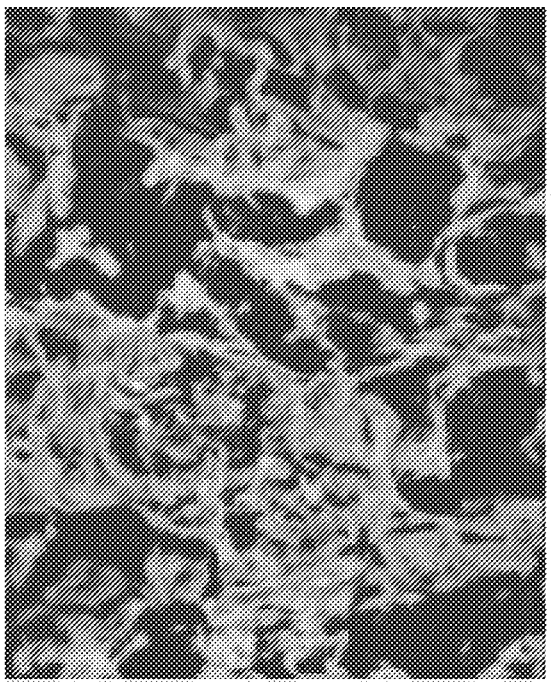
Figure 1Q:
Figure 1N:
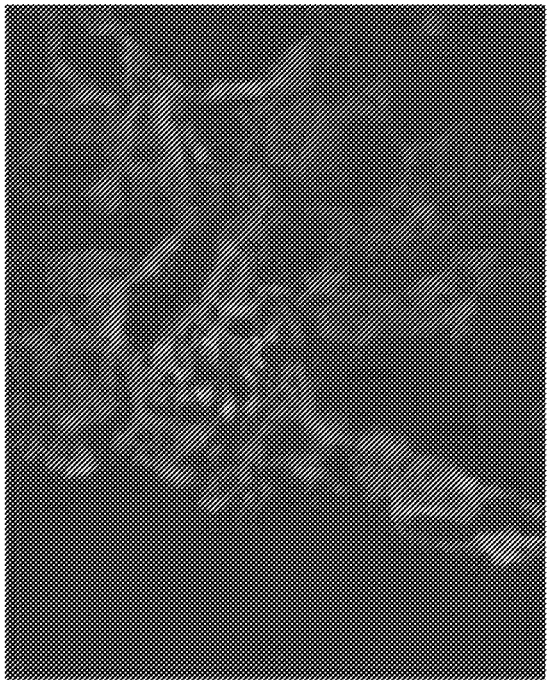
Figure 1P:
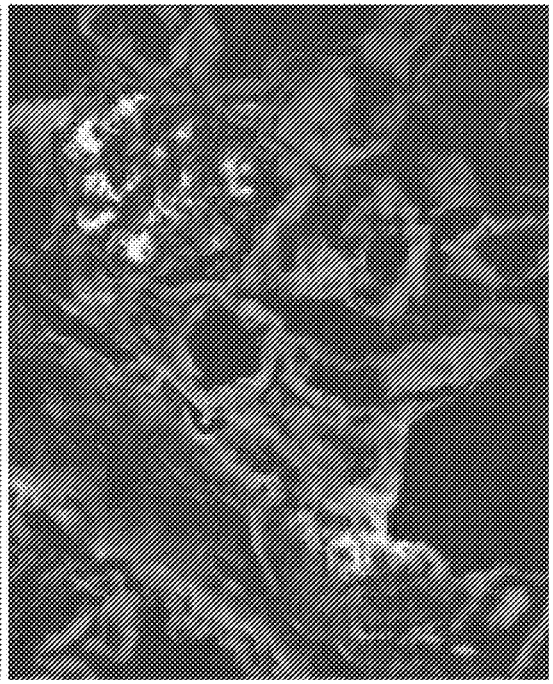

Examining the kidney, we have found that the complete absence of Rab3A results in a subtle glomerular phenotype, clinically characterized by macroalbuminuria starting early and persisting over time (FIG. 1a). Until the age of three months, histological alterations are evident only by electron microscopy, with glomerular lesions that are common to a variety of human nephropathies, such as segmental podocyte foot process effacement and a certain degree of mesangial expansion and proliferation (FIG. 1b-e). A parallel focal and segmental decrease of specific podocyte proteins, 4 namely nephrin, podocin (FIG. 1f-i), alpha-actinin, and ZO-1, can be detected by immunohistochemistry.

By the age of six months, mesangial expansion is evident even by light microscopy in about 50% of glomeruli (FIG. 1j-m), corresponding to an increase of matrix proteins, such as Tenascin C and collagen type I (FIG. 1n-q).

In the interstitium, scattered stalks of fibrosis, not accompanied by evident leukocyte infiltration, are present by the age of 9 months.

Nephropathy does not seem to affect the life span of these animals, but absence of Rab3A does induce glomerular alterations, indicating a role for this protein in the normal glomerular homeostasis.

Rab3A and Human Proteinuric Diseases

In order to examine potential changes of Rab3A in human disease, we have studied 101 renal biopsies by immunohistochemistry and by molecular probe analysis. In human nephropathies Rab3A expression is highly variable, independent of disease diagnosis. The immunohistochemical expression level can be similar to that of normal control kidneys[5], showing a comma-like pattern of positivity along the glomerular basement membrane (FIG. 2a), or be alternatively up- or downregulated (FIG. 2b-c).

Figure 2D:
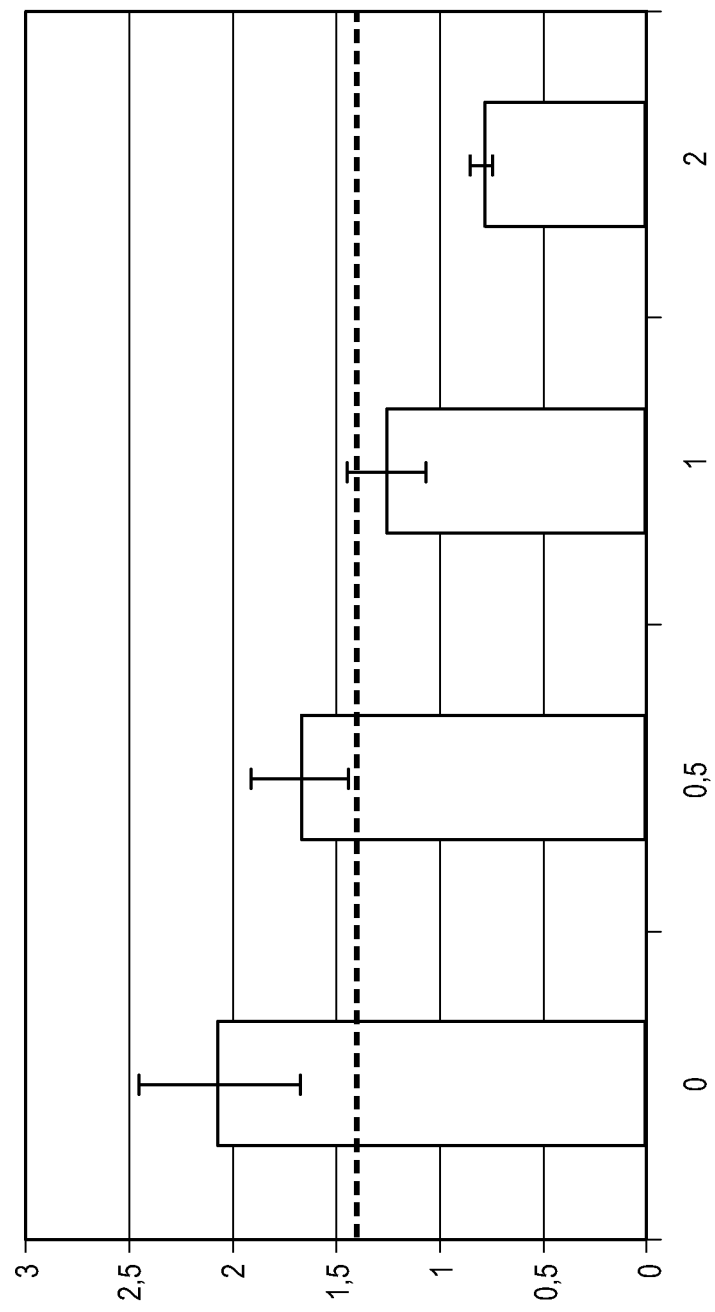

In contrast to the considerable variation between biopsies, the staining pattern in individual cases is rather homogeneous among different glomeruli. Furthermore, the overall staining for Rab3A highly correlates with renal function (FIG. 2d). Real time quantitative RT-PCR analysis confirms the immunohistological changes on the glomerular level of mRNA (FIG. 2e).

RAB3A Gene Analysis

Human RAB3A gene maps to 19p13.2. It covers approximately 7 kb on the minus strand and has 5 introns and 5 (4 coding) exons. Rab3A, as well as most Rab proteins, is highly conserved among species, showing more than 70% similarity with *S. cerevisiae* and *C. elegans* (http://www.ncbi.nlm.nih.gov/UniGene/clust.cgi?ORG=Hs&CID=27744).

[AC068499. *Homo sapiens* chromosome 19]

Several already published SNPs do not seem to be linked to any human disease (http://www.ncbi.nlm.nih.gov/SNP/snp_ref.cgi?locusId=5864) and a recent study has failed to find an association between RAB3A variants and autism, but patients with nephropathies have never been considered. We have therefore examined RAB3A genomic sequence in 50 proteinuric patients and 10 normal subjects.

Our preliminary results confirm the wide presence in our population (both controls and disease) of the previously published SNPs. Moreover, we have found only in sporadic nephropathic cases 6 not yet published intronic SNPs and 2 exonic SNPs, the latter responsible for amino acid variation and both expressed in heterozygosity (FIG. 2f).

The first exonic SNP, located in exon 1, at nucleotide 27363, is a G/T transversion that causes Arg66Ser mutation in a case of IgA nephropathy.

Figure 2G:
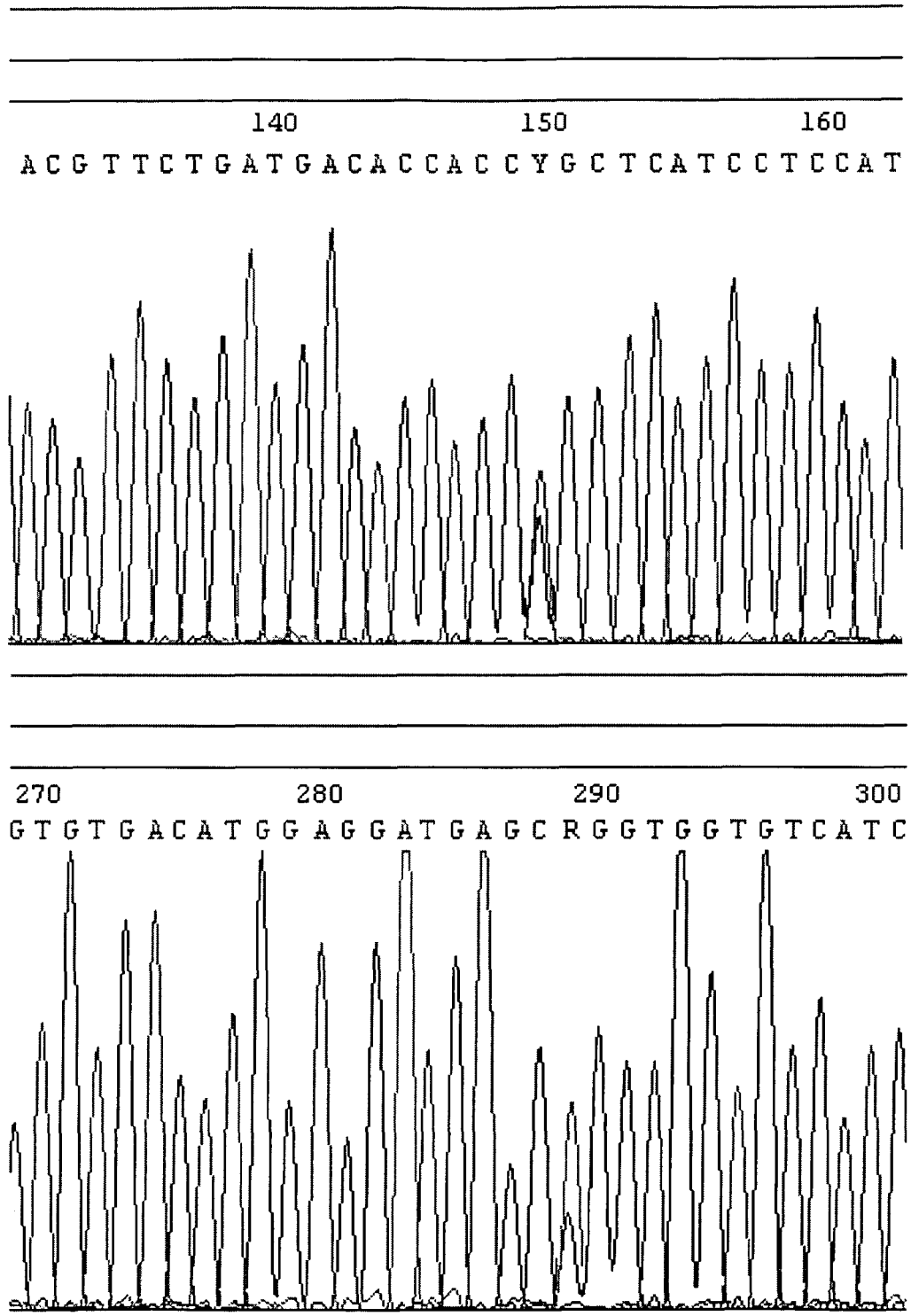

The second one, located in exon 3, at nucleotide 23587, is a C/T transition that causes Arg143Gln mutation and is present in a case of lupus nephritis (FIG. 2g).

Figure 2H:
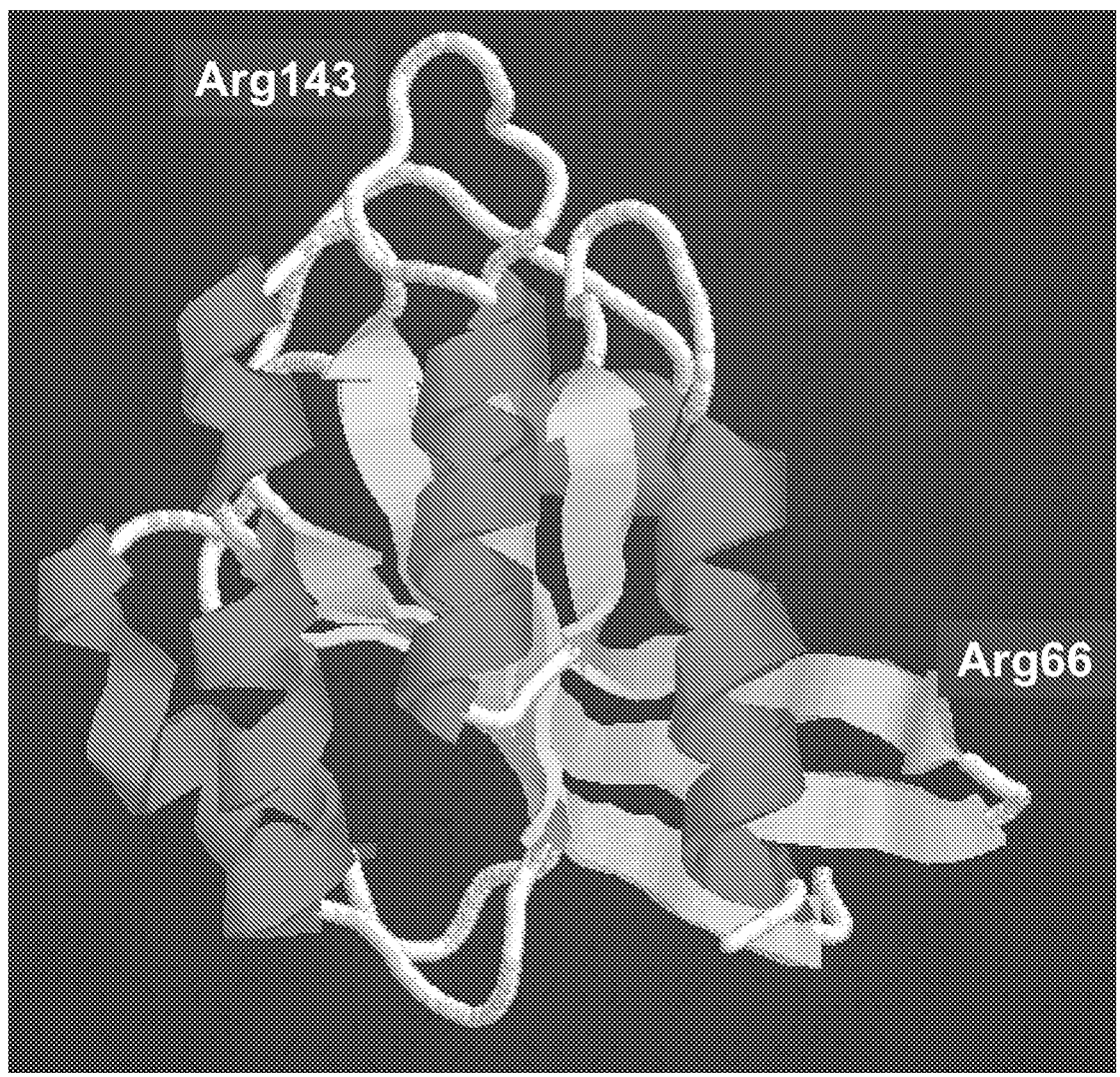

Both the mutated Arginines are phylogenetically well conserved in Rab3A. Moreover, Arg143 (FIG. 2h) is part of a connecting loop, and the change to Glutamine could affect the stability of the loop and produce a conformational modification of the molecule.

Arg66, that is located on the beta2 sheet (FIG. 2h), has been reported to be involved in binding of calcium-calmodulin[3]. The amino acid is conserved only in the so-called exocytic Rabs (such as Rab3 and Rab27), and its change could impair the exocytic function of the molecule.

Figure 2I:
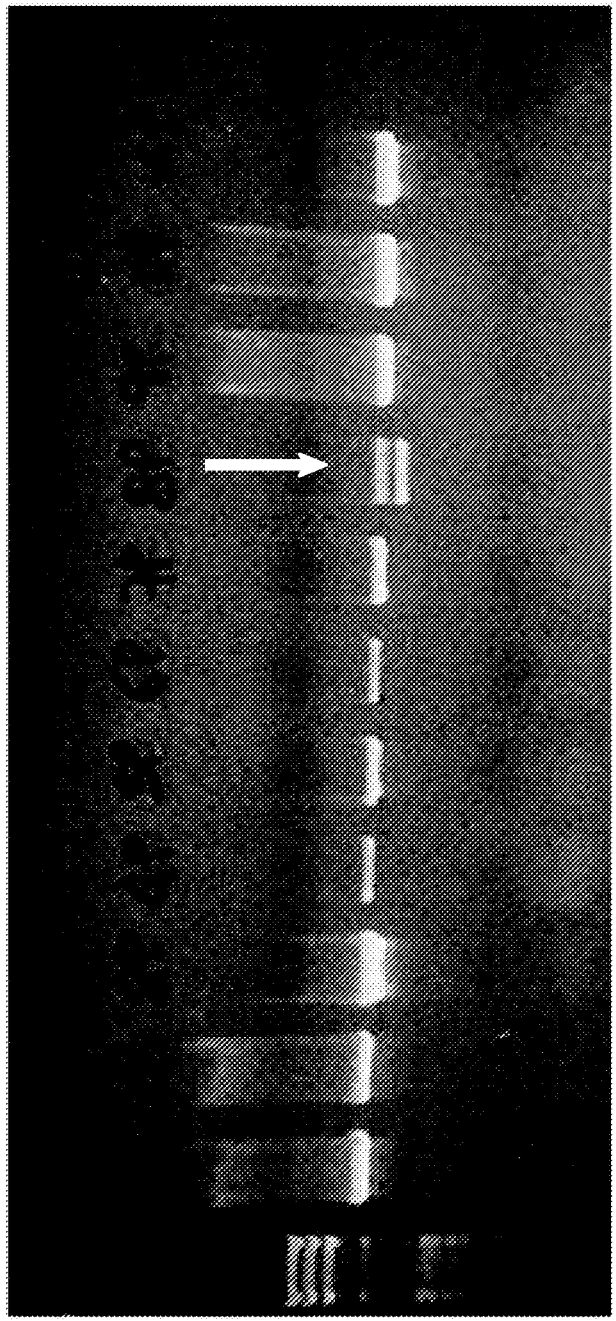

We have also analyzed the full-length mRNA extracted from microdissected glomeruli of 15 patients with various nephropathies. One of them, affected by type II diabetic nephropathy, has shown on agarose gel a different pattern with two bands, one shorter than the expected length (FIG. 2i). By sequencing, the shorter band has revealed a truncation of 125 nucleotides, producing a frame shift and an abnormal stop codon at nucleotide 361. The expected protein from this mRNA would be 120 aa long instead of the normal 221, with a substitution of 4 aa (117-120), and the loss of two complementary determining regions (CDR), the C-terminal hypervariable region and the 2 terminal cysteines. This truncated protein can not be functional, because it lacks important domains of the molecule: the CDR and the C-terminal hypervariable region are in fact major determinants of 6 functional effector specificity and the two C-terminal cysteins, being isoprenylated, allow the membrane vesicle binding[11].

From these data, we can conclude that Rab3A is altered in proteinuric diseases and variants of the molecule can be found in human nephropathies.

The Role of Rab3A and Other Related Proteins in Podocytes: Similarities with Neurons Podocytes and neurons have several morphological and biochemical similarities: both are highly arborized, have a common cytoskeletal organization[12, 13], and share several expression restricted proteins, such as nephrin[14], densin[15], GLEPP-1[16], the amino acid transporters CAT3 and EAAT2[17], and the cytoskeletal proteins synaptopodin[18] and drebrin[19].

Figure 3A:
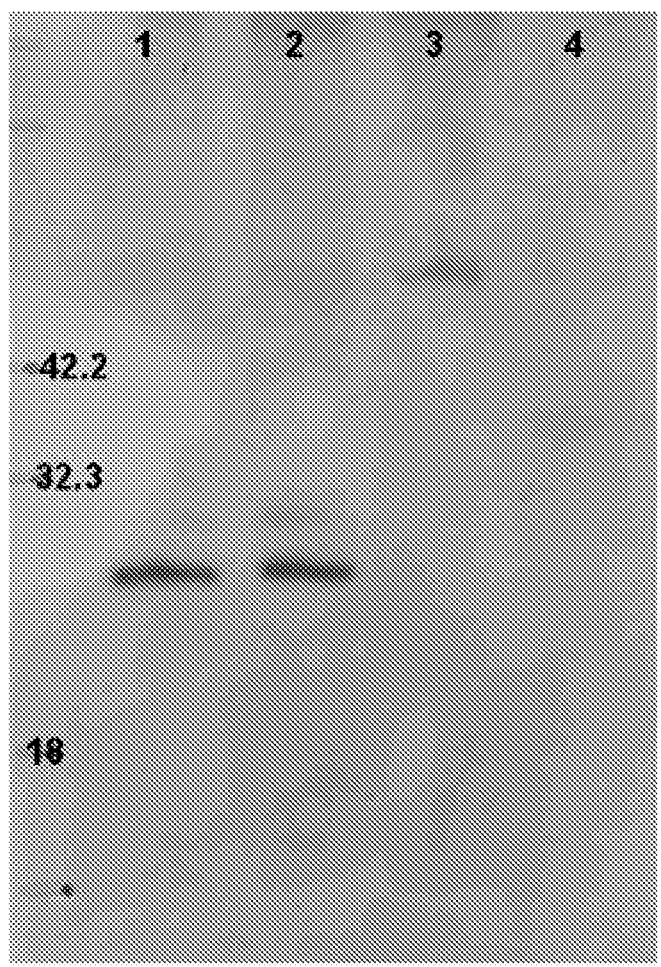

To understand the possible role played by Rab3A in podocytes, we have immunoprecipitated Rab3A from normal mouse kidney glomeruli and normal mouse brain (FIG. 3a). After SDS-PAGE electrophoresis and silver staining, six bands have been selected on the basis of their apparent overexpression in material coming from glomeruli compared to brain immunoprecipitates. The bands have been trypsin-digested and analyzed by mass spectrometry.

Maldi-TOFF analysis has not demonstrated coimmunoprecipitation of Rab3A with any specific podocyte protein. It has however shown the coimmunoprecipitation of Rab3A with molecules involved in neuronal processes of synaptic exocytosis, such as synaptotagmin 1, glycine-, glutamate-, thienylcyclohexylpiperidine-binding protein, or with molecules involved in the cellular cycle of Rab3A, such as Rab GDP-dissociation inhibitor (Rab GDI). Moreover, we found coimmunoprecipitation with mitochondrial molecules (namely ATP5b and ATP synthase H+transporting F1 complex, beta subunit), that seem to suggest a possible mitochondrial localization of Rab3A, that may have importance in oxidative damage and in regulating the cell respiratory burst or may be linked to the energy required for highly regulated exocytosis.

Figure 3B:
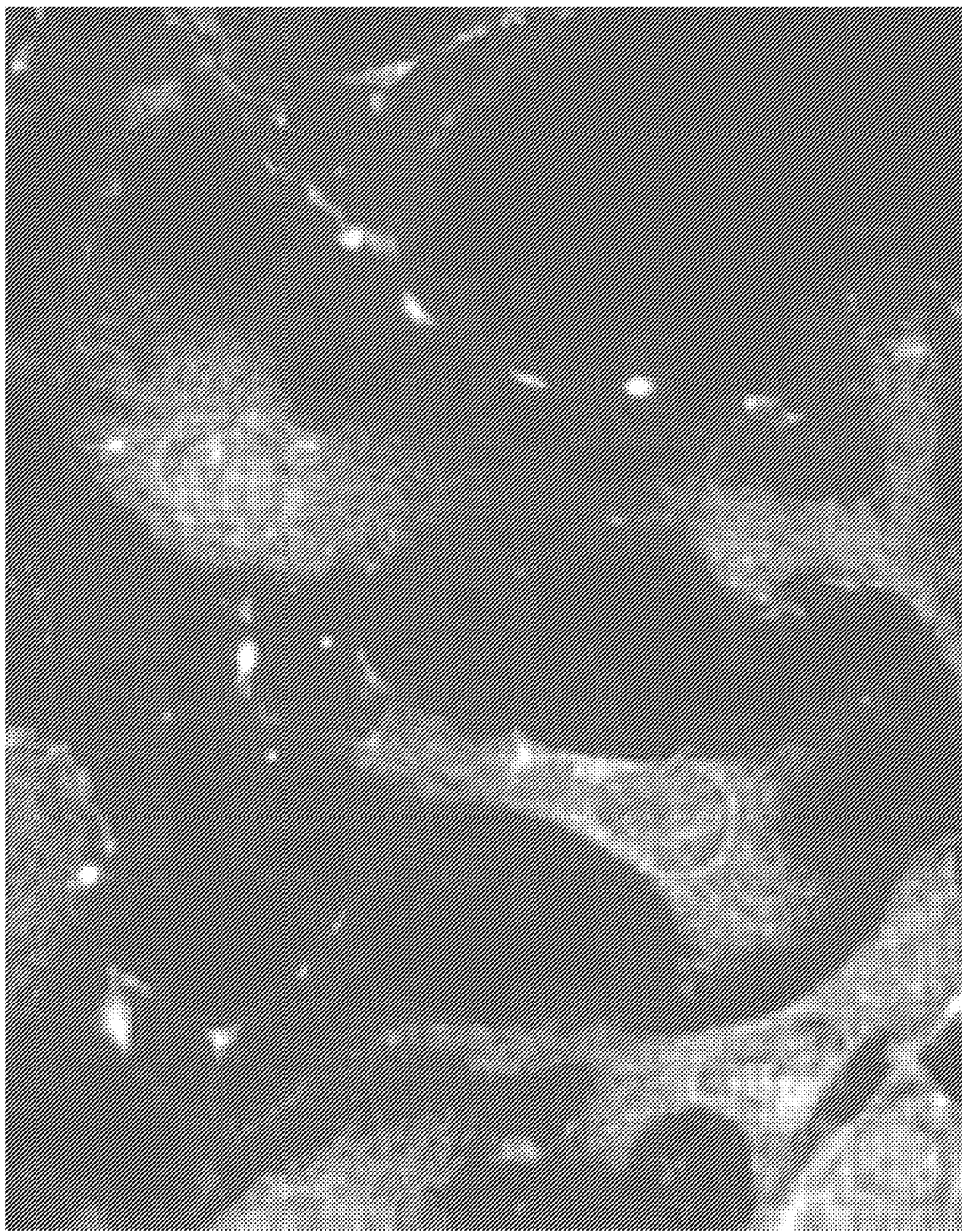
Figures 3C, 3D, 3E, 3F:
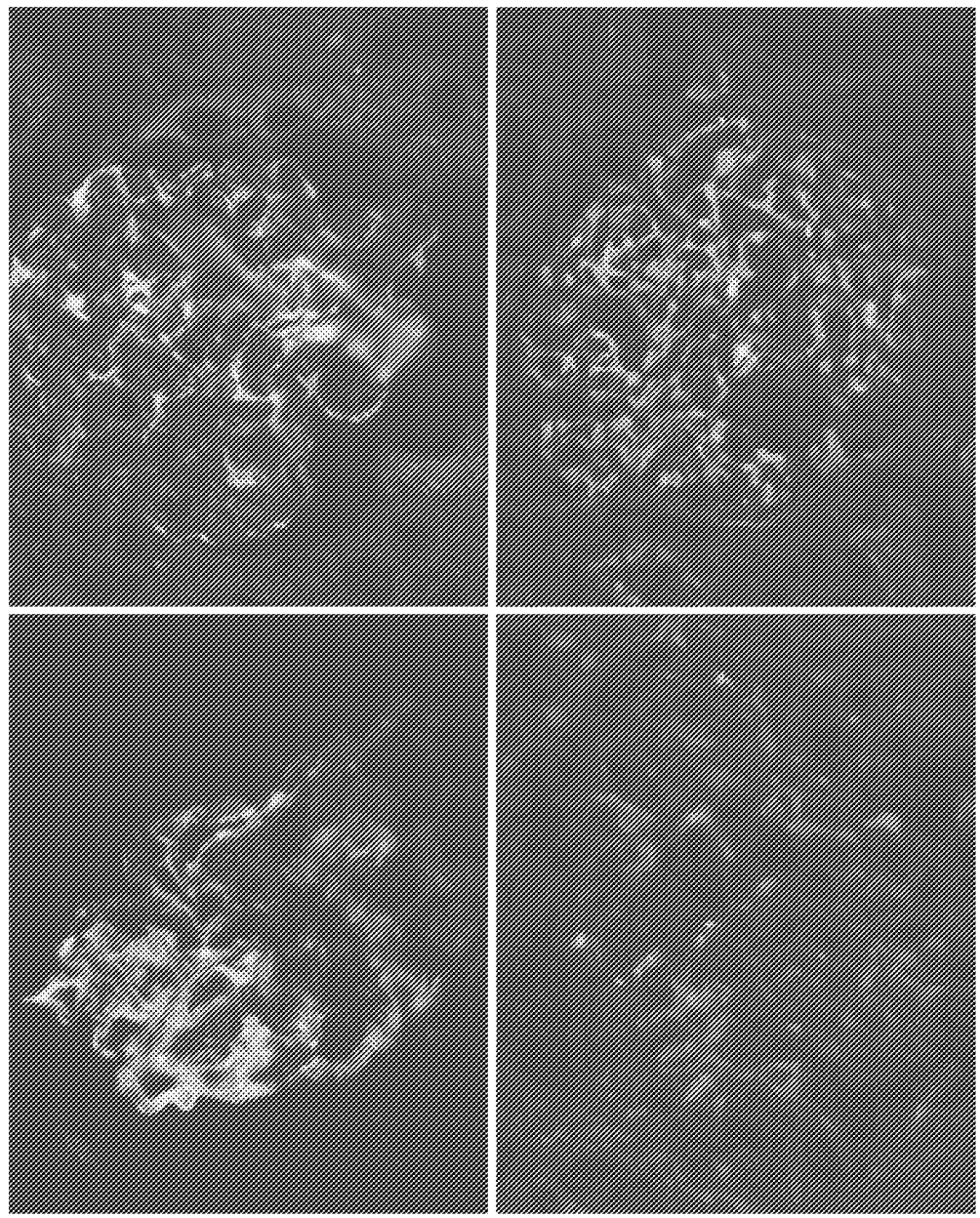
Figure 3G:
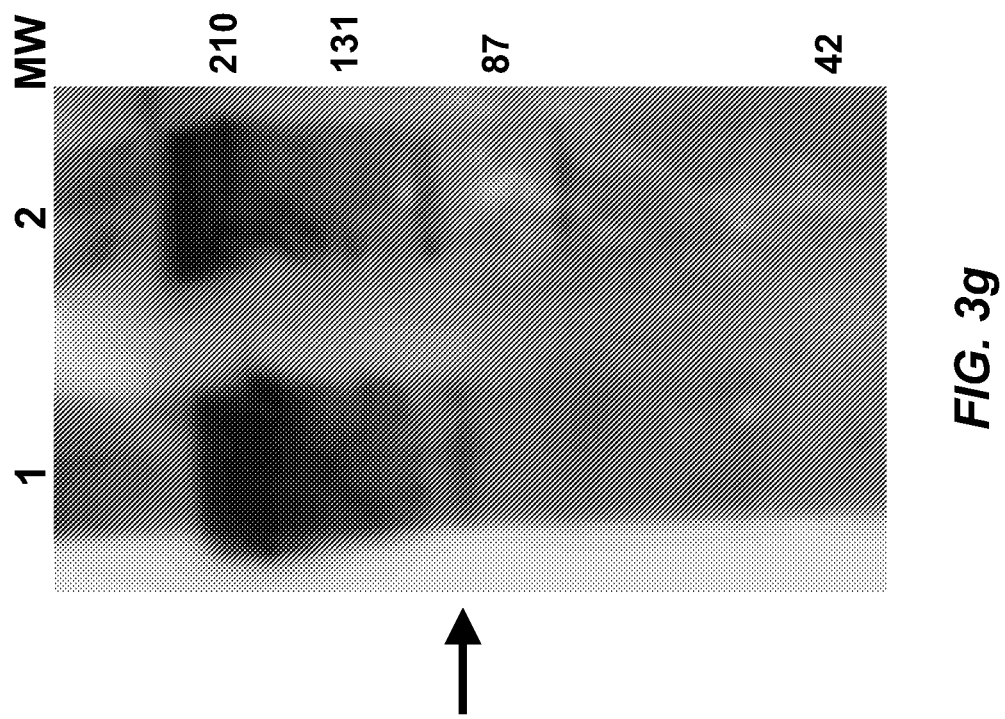

Starting from these data and from the notion that in the brain Rab3A null mice have prevalent defects in glutamatergic synapses[8, 20], we have first investigated the possible presence of glutamate in podocyte cell cultures. By double staining, a co-localization of glutamate with Rab3A is evident, especially localized to podocyte processes (FIG. 3b). Subsequently, we have detected the vesicular glutamate transporter Vglut1 and the vacuolar proton pump (V-ATPase) in cultured podocytes and we have confirmed the presence of glutamate in normal mouse and human glomeruli, together with metabotropic and ionotropic glutamate 7 receptors. All the molecules are mainly localized along the glomerular basement membrane (FIG. 3c-3f). Presence of the glutamate NMDA-1 receptor from a mouse glomerular lysate has been also confirmed by Western Blot analysis (FIG. 3g) and coimmunoprecipitation experiments have shown that NMDA-1 coimmunoprecipitates with nephrin, the most important molecule in the slit diaphragm.

We have next examined if podocytes are able to release and take up glutamate. Alpha-latrotoxin is a potent neurotoxin from black widow spider venom, widely used to provoke neurotransmitter release from synaptic vesicles[21]. At subnanomolar and nanomolar concentrations, α-latrotoxin stimulates continuous and bursting synaptic exocytosis respectively, whereas higher concentrations (>10 nM are highly damaging for cell membranes, behaving like a detergent[22].

Figure 4A:
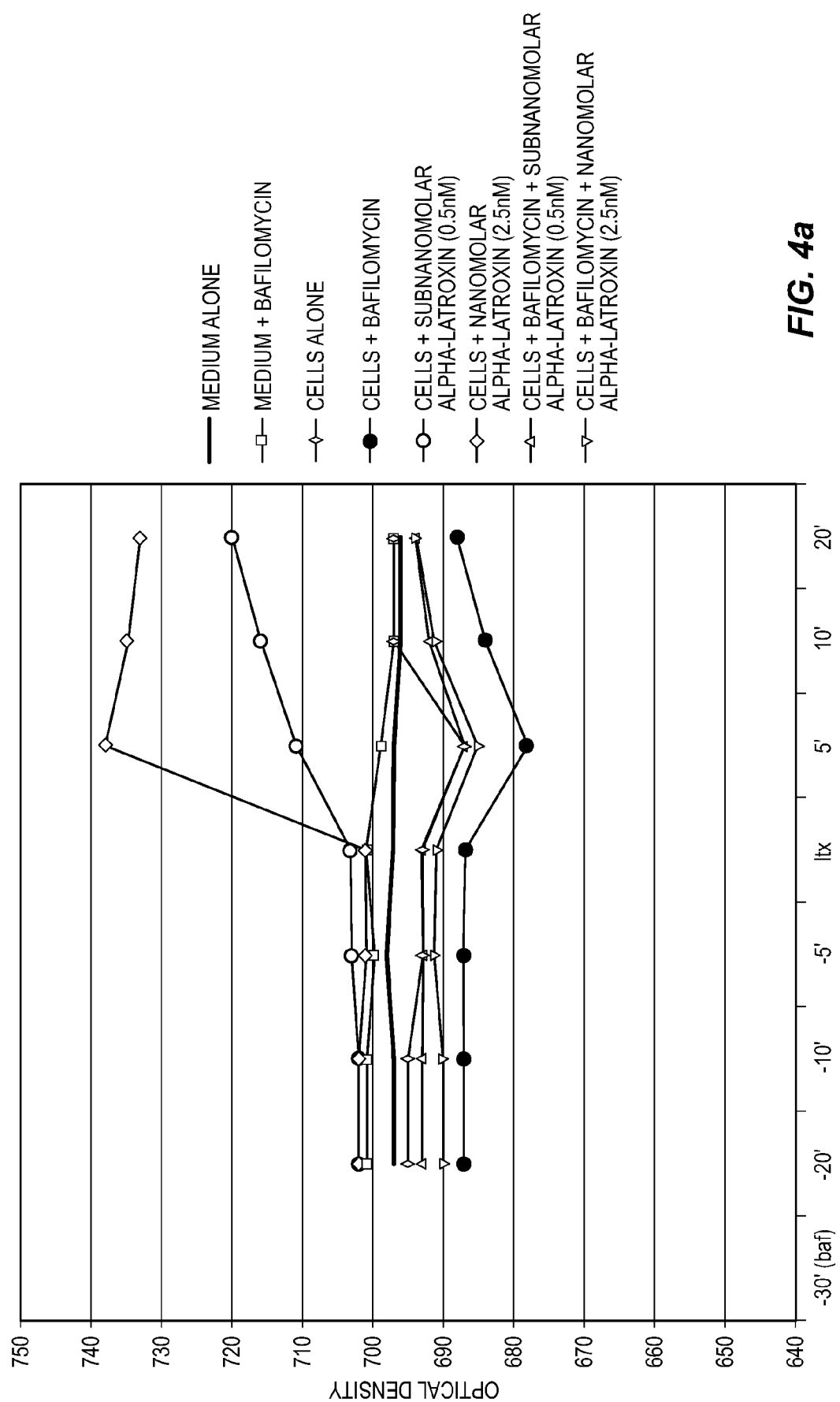
Figures 4B, 4C, 4D, 4E:
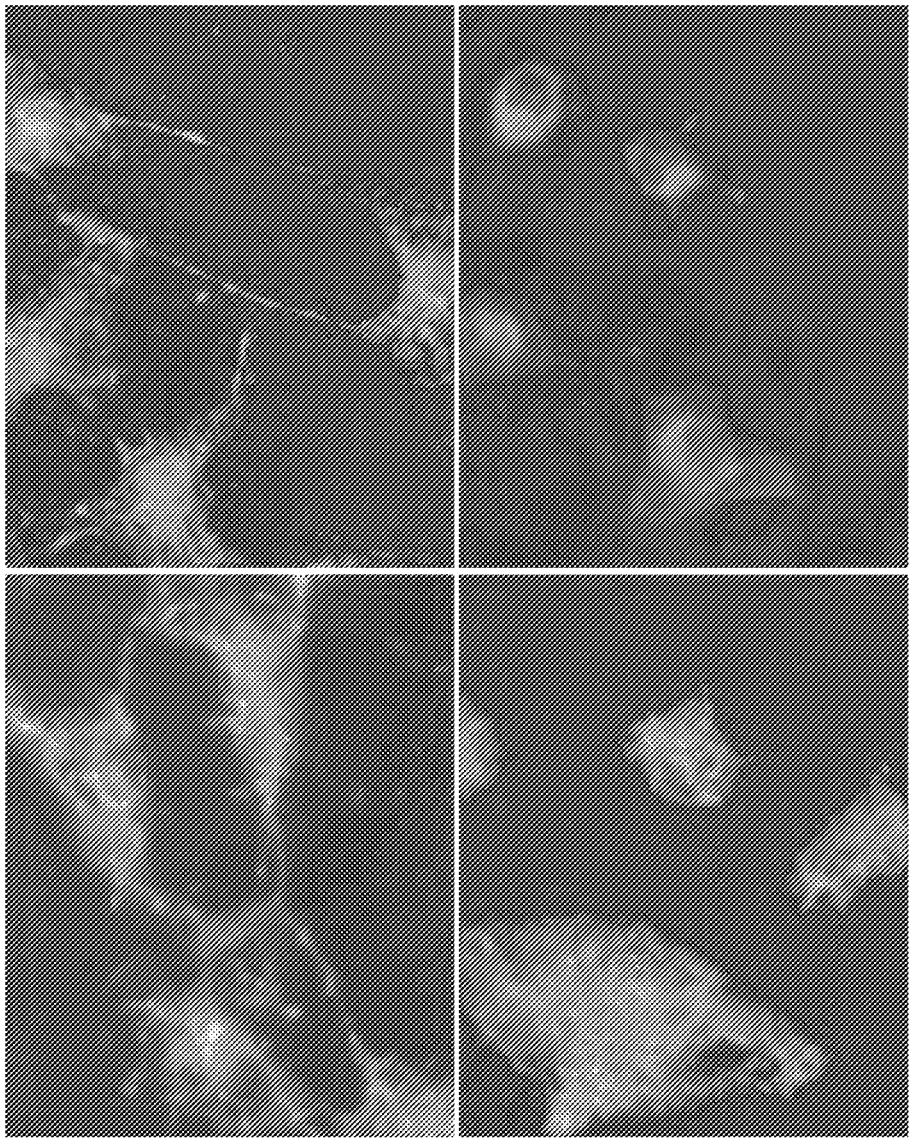

We have therefore applied subnanomolar (0.5 nM) and nanomolar (2.5 nM) α-latrotoxin on cultured podocytes, and found that glutamate release is actually taking place at both concentrations (FIG. 4a).

We have also observed by immunohistochemistry a redistribution of Rab3A and the disappearance of most glutamate from cell processes after nanomolar α-latrotoxin treatment (FIG. 4b-e). These data provide two pieces of information:

the demonstration that glutamate is released by podocytes and the indirect evidence of α-latrotoxin receptors on these cells.

Figure 4F:
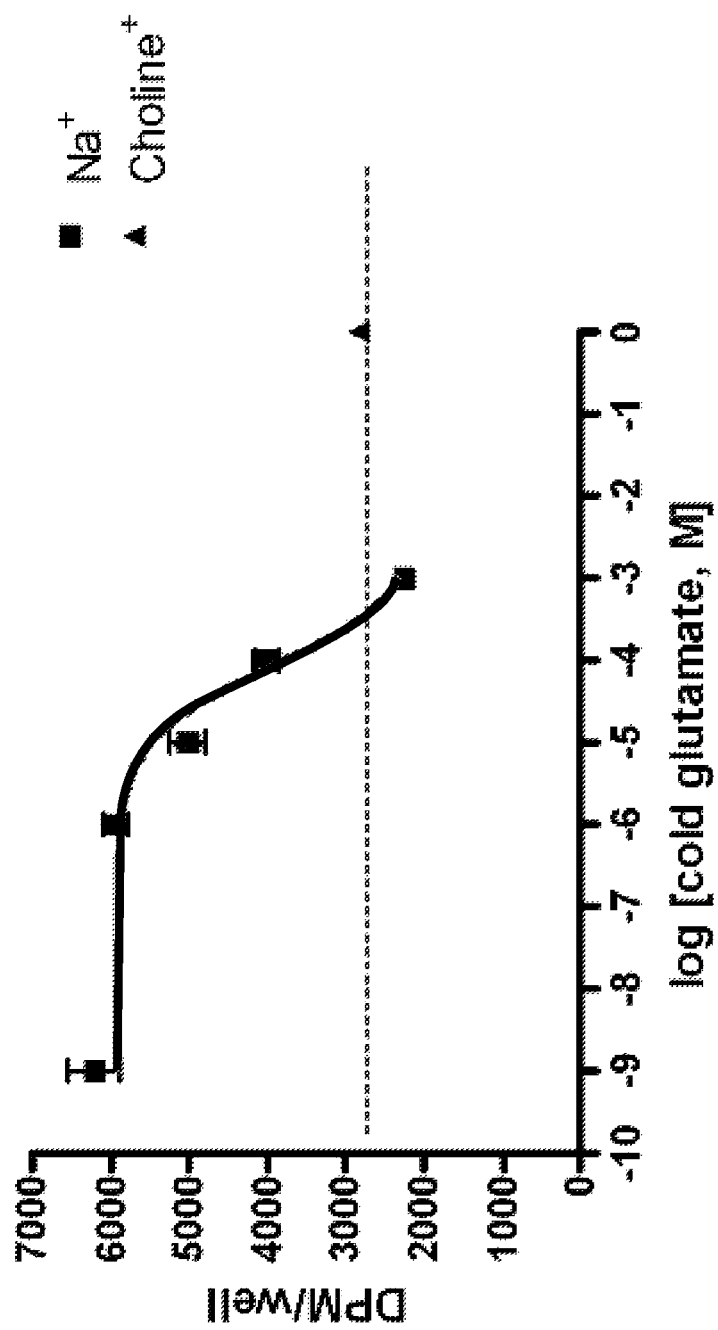
Figure 5:
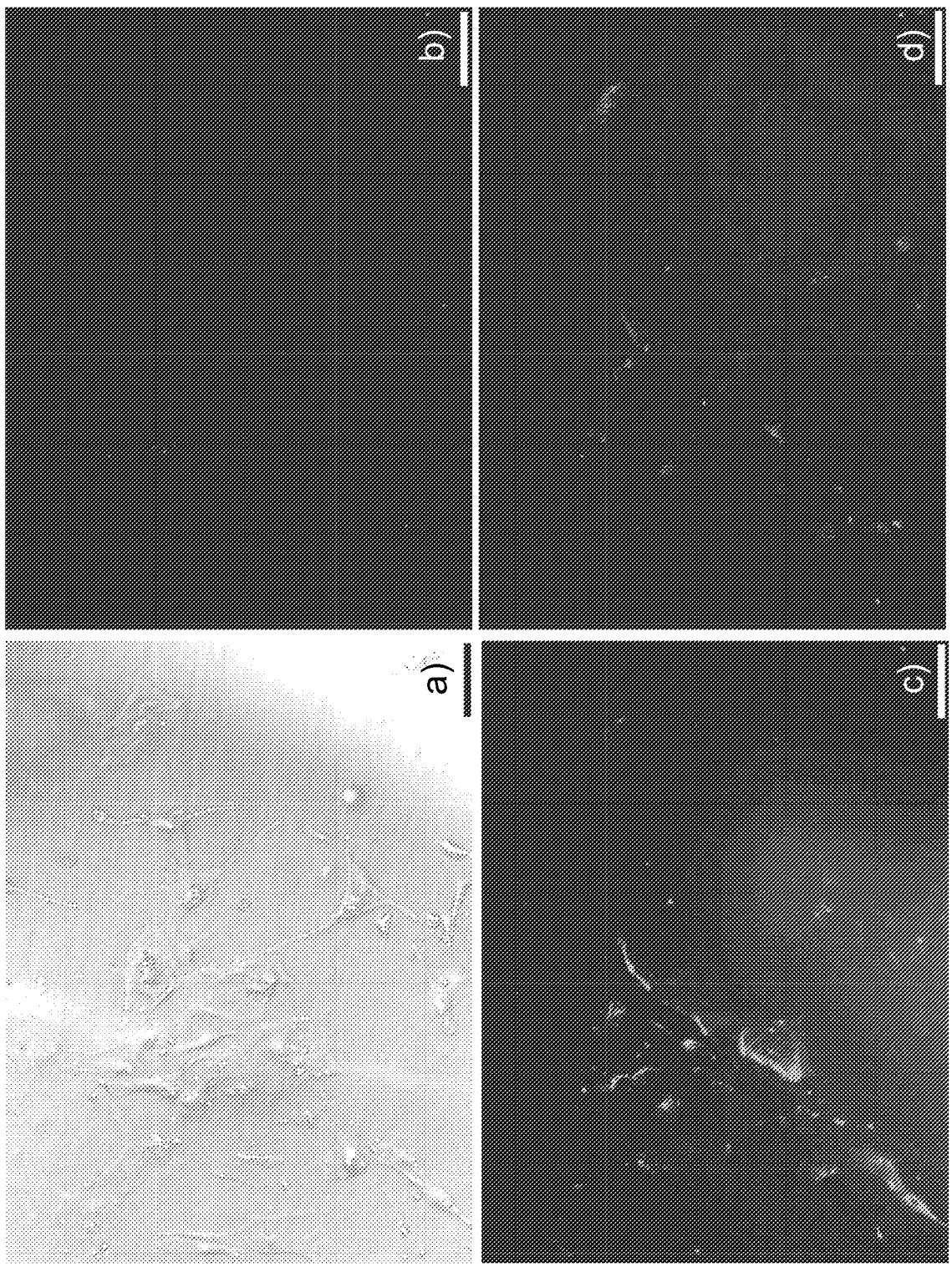
FIG. 5 shows synaptic recycling.
Figure 6:
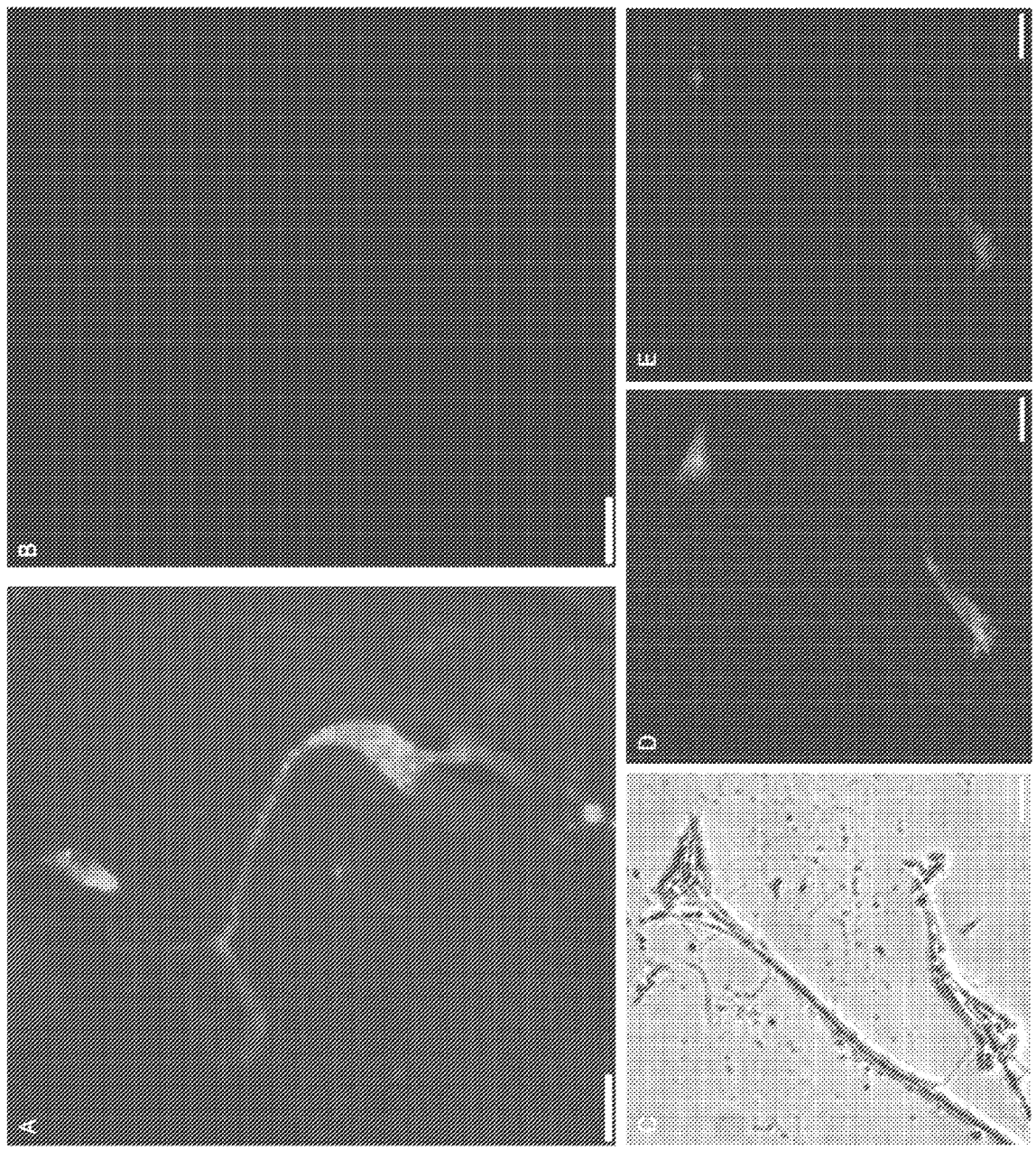
FIG. 6 shows podocytes incubated with an antibody directed against a luminal epitope of synaptotagmin 1.

Cultured podocytes have also shown in our hands a measurable accumulation of L-glutamate, whose characteristics (Na+-dependency and Km of 83 μM) are suggestive of an uptake through Lglutamate transporters, with an estimated Vmax of about 2 pmol/min/well (FIG. 4f).

The recycling of synaptic vesicles in nerve terminals is a complex multistep process, whose investigation has been made feasible by the use of styryl dyes. These molecules, that reversibly insert into the surface of lipid membranes, have no fluorescent properties in aqueous solution, but become intensely fluorescent upon membrane binding, allowing a labelling of recycling synaptic vesicles that is easily detectable by fluorescence microscopy. Actually, primary podocytes looked able to accumulate the styryl dye FM1-43 a few seconds after a first α-latrotoxin stimulus, and to almost completely discharge the dye after a second α-latrotoxin stimulation, features that support the existence in these cells of a synaptic vesicle recycling (FIG. 5A-D).

To further prove the synaptic nature of these vesicles, we incubated podocytes in vivo with an antibody directed against a luminal epitope of synaptotagmin 1, that becomes exposed to the extracellular space as a result of exocytosis, then is internalized during the next round endocytosis. After fixation, cells were then probed with another antibody against the C2 domain of synaptotagmin 1, that is present on the outer aspect of the vesicle. The precise colocalization of these markers definitely demonstrated that an activity of synaptic vesicle exocytosis and recycling is going on in these cells (FIG. 6A-E).

Figures 7A, 7B, 7C:
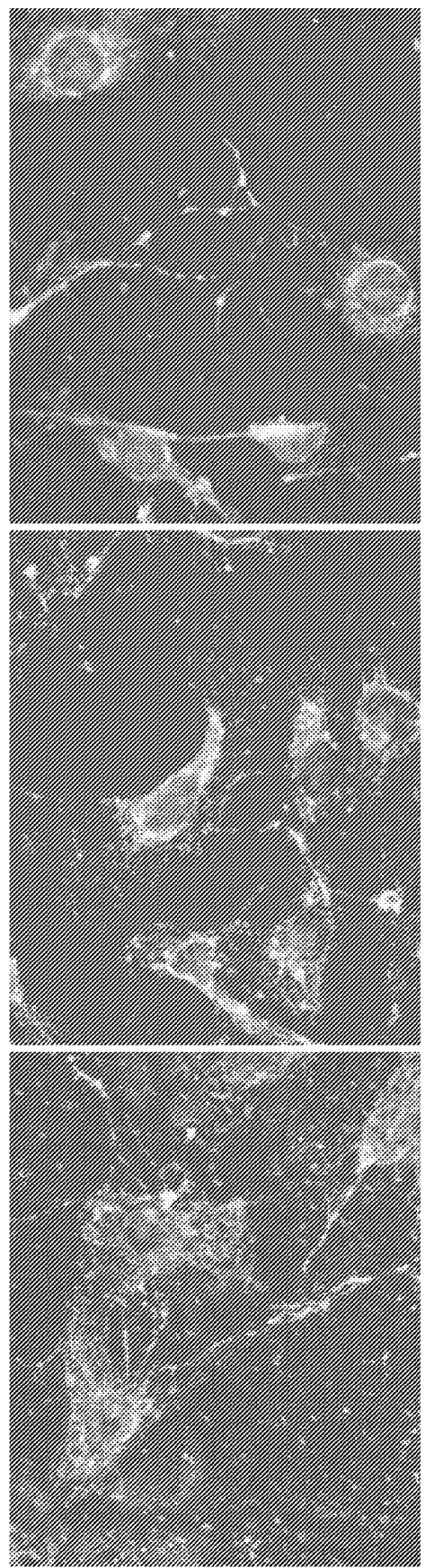
FIG. 7 shows synaptic molecules at podocyte level. Panel a)-c): Cultured mouse podocytes are stained by antibodies directed against the synaptic molecules syntaxin (a), synaptophysin (b), and synapsin (c) (indirect immunofluorescence, 450×).

We have then tried to get information about the possible presence of synaptic molecules at glomerular level. First we have found by immunohistochemistry that several proteins, such as syntaxin, synaptophysin, synapsin, and SAP102, are detectable as small scattered dots along the glomerular capillary wall. They can be also observed in podocyte cell cultures, along the processes or at the edge of the cell body (FIG. 7a-c).

Discussion

Glomerular podocytes, the most important players in the glomerular filtration barrier, are highly differentiated cells with a complex ramified structure: few major processes departing from the cell body give rise on both sides to many fine pedicels, that interdigitate with corresponding projections of neighbouring cells[23], with few finger-like protrusions floating within the Bowman's space[24]. This elaborate shape is supposed to be essential for many activities played in concert not only with neighbouring podocytes, but also with endothelial and mesangial cells. To achieve this result, it is reasonable to imagine that podocytes need a fast and precise way to talk to each other and to the other glomerular cells. It has been recently demonstrated by several authors (reviewed by T. Benzing[25]) that both the slit diaphragm and the basal domain of the foot processes are highly dynamic signalling domains. Our results, showing that glomeruli synthesize most if not all neuron-specific molecules, and that podocytes are able to release and take up glutamate, the prominent excitatory neurotransmitter in the brain, strongly suggest that signals are triggered in a proper synaptic way.

Several published results seem in agreement with our data. The group of Pavenstädt has for instance demonstrated that a depolarization, due to increase of free intracellular calcium, occurs by exposure of podocytes to the neurotransmitters acetylcholine and norepinephrine via their specific receptors M5 and D1-like[26,27]. Moreover, foot processes regularly contain several coated vesicles[28], at least some of them positive for Rab3A, as we have shown by immunogold electron microscopy[5]. Furthermore, very recently, Miyauchi et al have found in podocyte foot processes the presence of the A and B isoforms of the synaptic vesicle protein SV2. In particular, the B isoform seems to be localized closely to nephrin and is down-regulated in puromycin aminonucleoside nephropathy (PAN) before the development of proteinura[29].

Our present work, apart from dissecting the role of Rab3A in podocytes, seems to complete the picture, showing that glomeruli synthesize all the components needed to build functional synapses. The relevance of highly regulated exocytic events to glomerular homeostasis is clearly demonstrated by the Rab3A knockout model. Four Rab3 isoforms (A, B, C, and D) are associated to exocytic vesicles and their redundancy has been recently clearly demonstrated[4]. Similar redundancy is likely to take place also in glomeruli. Nonetheless, the rescue operated by the other isoforms seems to be only partial, because, as it happens in the brain, the absence of the A isoform at glomerular level is relevant to the phenotype.

Based on our working hypothesis of synaptic transmission in podocytes, the slit diaphragm molecules could be regarded as synaptic adhesion molecules. Surprisingly, when considered in this way, many already described features of the slit diaphragm fall into place. For example, all neuron-neuron synapses bear at least one cadherin-like adhesion molecule and at least one immunoglobulin superfamily molecule, with cadherins mainly mediating homophylic adhesion, whereas both homo- and heterophylic interactions are established among Ig-like proteins[30]. The slit diaphragm is precisely composed by Ig-like molecules, such as nephrin and NEPH1, making both homophilic and heterophilic interactions[31], and cadherin molecules, such as P-cadherin[32], and the protocadherin FAT[33].

As for their function, apart from promoting the stability of synapses, many data support the role of synaptic adhesion molecules in target recognition, i.e. to help in choosing the right synaptic partners from a network of processes[34]. Interdigitating podocyte foot processes likely use the same mechanism to find their right place and partner. In this respect, it seems worth noting that SYG-1, the C. elegans orthologue of NEPH-1, is a molecule that has been isolated in a genetic screen for mutants defective in synaptic positioning[35]. The profound alterations in homozygous knock-out mice generated by targeted inactivation of NPHS1 or NEPH1 genes[14, 36] could be explained as a failure in target recognition as well. Synaptic adhesion molecules are believed also to regulate synapse maturation and plasticity[30]. Several adhesion molecules regulate for instance dendritic spine morphology, that is known to profoundly change in relation to synaptic activity or during degenerative diseases[37, 38]. The fingerlike protrusions that characterize foot processes when observed by scanning electron microscopy are highly reminiscent of dendritic spines and their profound remodelling can be observed during nephropathies[24].

Our "synaptic view" also fits with the adhesive properties of the basal cell membrane (the sole plate) of foot processes with the glomerular basement membrane. In this case, a kind of neuromuscular junction comes to mind, first because of the presence of a basal lamina, second because of its composition by integrins and dystroglycans[39]. Agrin, that is considered a critical nerve-derived organizer of postsynaptic differentiation in neuromuscular junctions[40], is produced by podocytes and is localized in the glomerular basement membrane[41]. The foot process basal domain is in contact with both endothelial and mesangial cells, and a failure of communication in case of damage could help to better explain endothelial and mesangial alterations that almost invariably are present in proteinuric diseases. On this subject, it is worth reminding the selective presence in the synaptic basement membrane of the neuromuscular junction and in the kidney glomerular basement membrane of the so-called synaptic laminin (s-laminin), now known as the laminin β2 chain.

Example 2

We have analyzed by electron microscopy the formation of junctions between podocyte foot processes in vitro, and found that they are morphologically similar to synapses, and that vesicles are always accompanying these junctions (FIG. 8-10).

By immunoprecipitation experiments, we have observed that the ionotropic glutamate receptor NMDA-1 (antibody from Abcam, Cambridge, UK) coimmunoprecipitates with nephrin (antibody provided by H. Holthofer, University of Helsinki) (FIG. 11).

Figure 13A:
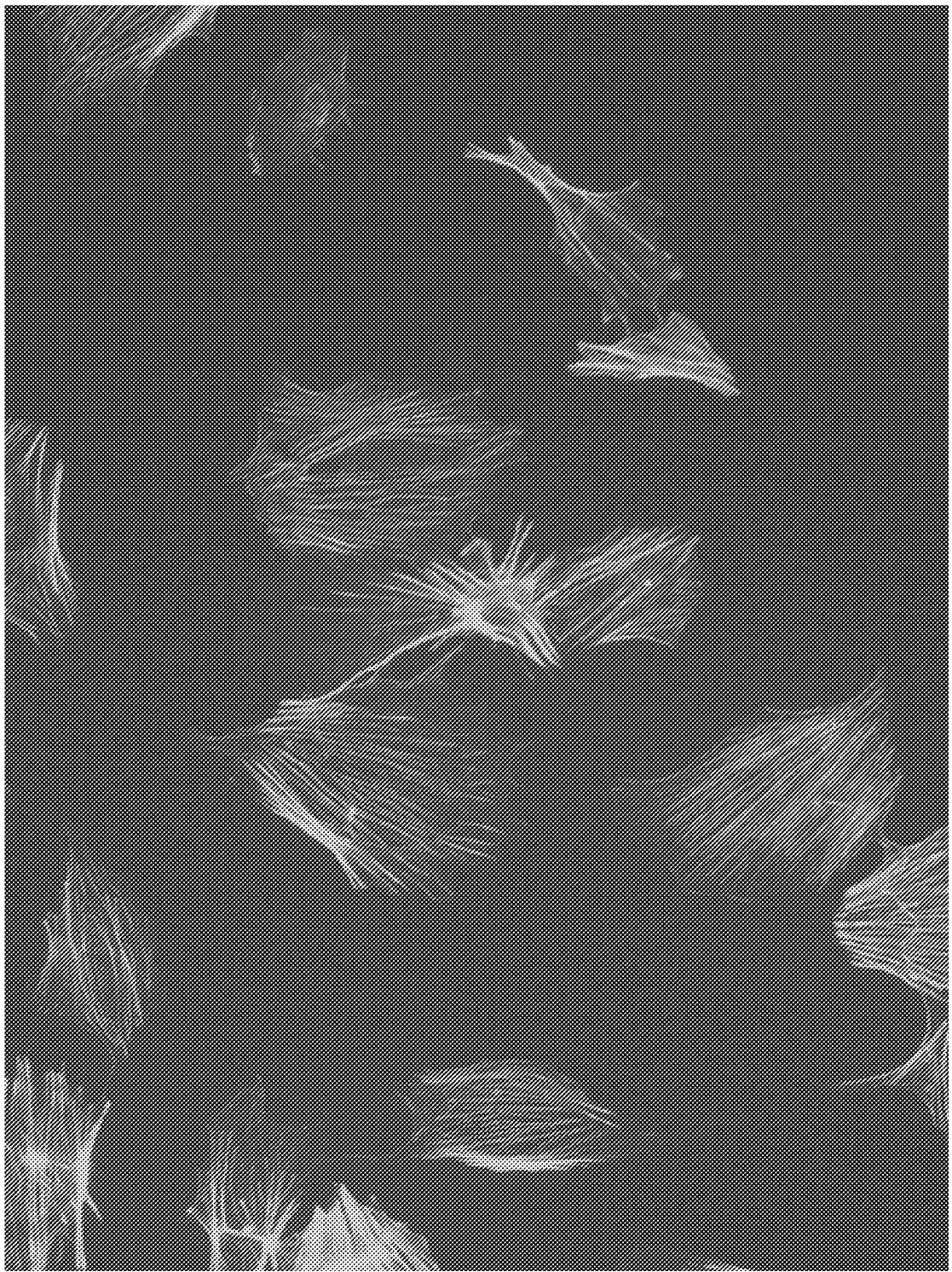
Figure 13B:

By immunohistochemistry, we have observed a variation of positivity, either increased or decreased, for other synaptic proteins, such as synapsin 1 (antibody from Abeam), and the ionotropic glutamate receptor NMDA-1 in a variety of human glomerulonephritis (FIG. 12). Furthermore, applying norketamine hydrochloride (an inhibitor of NMDA receptor), to podocytes in culture, results in a profound alteration of the actin cytoskeleton, demonstrating the importance of glutamate signalling for podocyte homeostasis (FIGS. 13A and 13B)

We have also repeated experiments of spontaneous and stimulated exocytosis, and have found
  a) that stimulated exocytosis can be induced also by 60 mM KCL, as it occurs in neurons
  b) that during alpha-latrotoxin and KCl stimulated exocytosis there is a rapid variation of the membrane potential, as demonstrated by the immediate accumulation and discharge of the specific fluorescent dye RH-414 (FIG. 14), and a rapid variation in calcium content, demonstrated by the fluorescent dye Fluo4 (FIGS. 15, 16), accompanied by variation of intra-vesicle pH, as documented by the fluorescent dye Lysosensor green, a marker of vesicle acidification (FIG. 17) (all fluorescent dyes are from Molecular Probes, Invitrogen, UK).
  c) that exocytotic events can be blocked by tetanus toxin, as it occurs in neuronal cells. From this second set of experiments, as an indirect result, we can assume that podocytes possess the tetanus toxin receptors.

Figure 18:
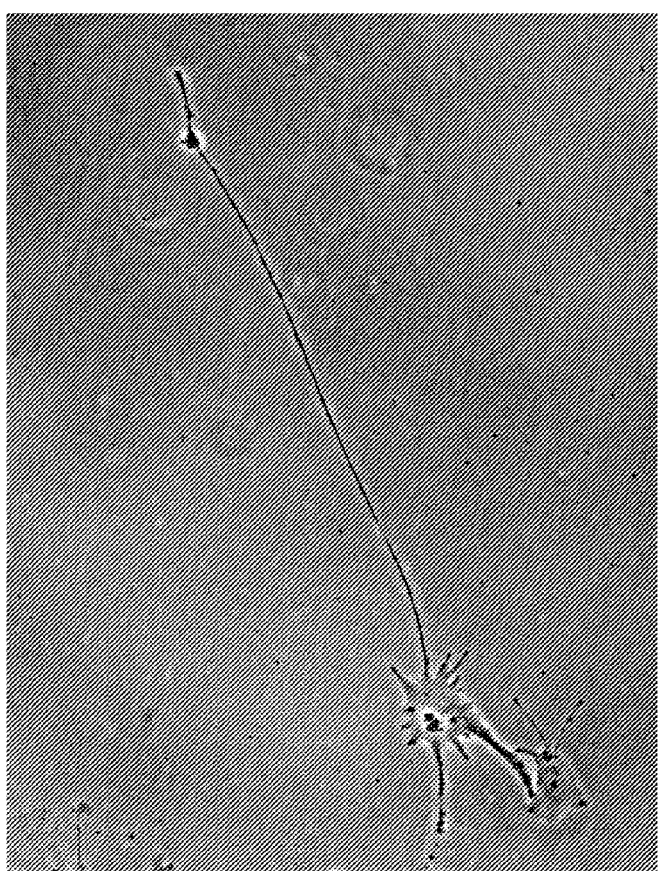
Figure 18:
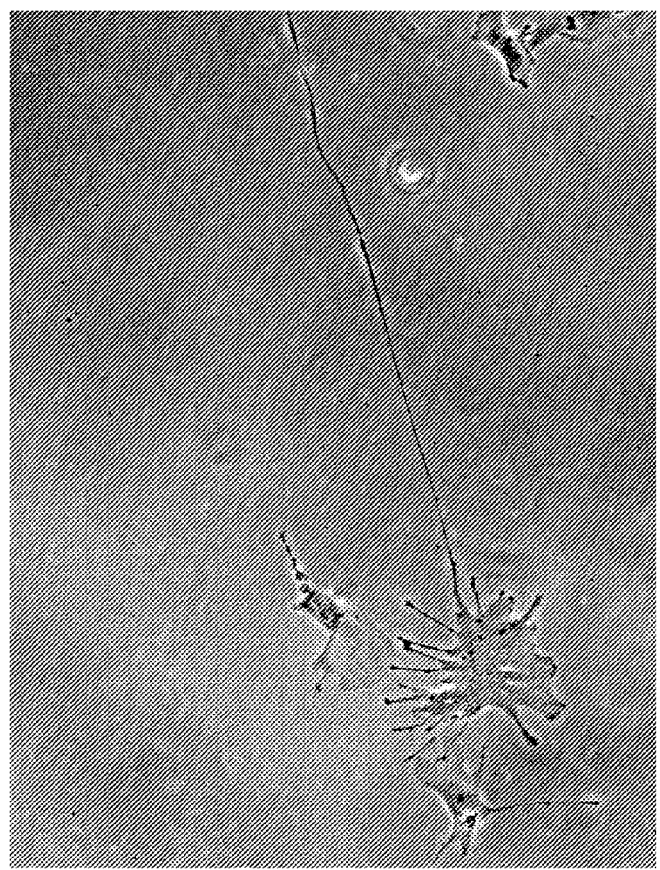

We have also observed that podocytes are sensitive to 250 ng/ml BDNF (Brain Derived Neurotrophic Factor) (Sigma): after 20 hour incubation with BDNF, in fact, the number of processes extending from the podocyte cell body are increased (FIG. 18). This indirectly means that podocytes possess BDNF receptors.

After observing in primary cultures that some podocytes are stained by GABA (FIG. 19), we have examined the expression of the enzyme that regulates the conversion of glutamate to GABA, namely glutamic acid decarboxylase (GAD). Among GAD isoforms, GAD67, that is considered brain-specific, looks more expressed in kidney glomeruli than GAD65, the more widely expressed isoform, once again confirming the neuron-glomerular axis of similarities (FIG. 20) (antibodies from Abcam). These results have been confirmed also from the mRNA side, that showed the transcription at glomerular level of the mRNA for several GABA receptors and GABA receptor associated molecules, so that from these data we can hypothesize that a GABAergic, inhibitory system of communication is also taking place in kidney glomeruli.

We have also started very recently to apply to glomeruli the method that has been established for synaptosome separation from brain (references 1-4).

Synaptosome Separation Method

The whole method is performed on ice.

After organ removal from 10 mice, hyppocampus is dissected from brain, whereas glomeruli are filter-separated from the kidney tissues (meshes 200-35 μm), then manually purified.

Material is manually homogenized to preserve the integrity of membranes in 20 ml buffer (Sucrose 0.32M, HEPES-NaOH 15 mM, $MgSO_4$ 1 mM, protease inhibitor cocktail, pH 7.4, where $MgSO_4$ is generally added to preserve synaptosome integrity) (all reagents from Sigma-Aldrich, Milan, Italy, but the protease inhibitor cocktail, that is from Roche), then centrifuged (2300 rpm×15'), and the supernatant kept on ice. The pellet, diluted in 10 ml buffer, is centrifuged again (2300 rpm×15').

Both supernatants are ultracentrifuged at 9000 rpm for 20', to obtain the so-called "crude mitochondrial pellet", that extracted from brain is known to contain free mitochondria and synaptosomes, together with membrane fragments and myelin fragments.

The remaining pellet is diluted in 2 ml of re-suspension buffer (Percoll 8.5% in sucrose 0.25M, HEPES-NaOH 5 mM, pH 7.4) (Sigma), then stratified on a Percoll gradient (12%-20%-30%) and centrifuged at 15500 rpm for 15'.

Synaptosomes can be collected from the lighter fractions, then Percoll is removed by adding 30 ml homogenizing buffer and centrifuging at 18000 rpm for 20'.

The pellet is then collected and fractions are stored in glutaraldehyde 2.5% for electron microscopy examination, or solubilized and sonicated for western blot analysis.

The results show that we were able to separate, from kidney glomeruli, some structures that show several similarities with synaptosomes, in particular they are bordered by a membrane, they contain vesicular structures, and they maintain a proper and structured adhesion to another membrane (FIGS. 21A, 21B). Furthermore, we could demonstrate by western blot analysis that these fractions are positive for synaptic vesicle molecules such as synaptotagmin-1 (FIG. 21C) and synapsin-1.

REFERENCES

1) Zerial, M., McBride, H. Rab proteins as membrane organizers. *Nat. Rev. Mol. Cell. Biol.* 2, 107-117 (2001).
2) Pereira-Leal, J. B., Seabra, M. C. Evolution of the Rab Family of Small GTP-binding Proteins *J. Mol. Biol.* 313, 889-901 (2001).
3) Darchen, F., Goud, B. Multiple aspects of Rab protein action in the secretory pathway: Focus on Rab3 and Rab6. *Biochimie* 82, 375-384 (2000).
4) Schlüter O. M., Schmitz F., Jahn R., Rosenmund C., Südhof T. C. A Complete Genetic Analysis of Neuronal Rab3 Function. *J. Neurosci.* 24, 66294637 (2004).
5) Rastaldi M. P., et al. Glomerular Podocytes Possess the Synaptic Vesicle Molecule Rab3A and Its Specific Effector Rabphilin-3a. *Am J Pathol* 163, 88W899 (2003).
6) Simons, M., Saffrich, R., Reiser, J., Mundel, P. Directed membrane transport is involved in process formation in cultured podocytes. *J Am Soc Nephrol* 10, 1633-1639 (1999).
7) Geppert, M., Goda, Y., Stevens, C. F., Sudhof, T. C. The small GTP-binding protein Rab3A regulates a late step in synaptic vesicle fusion. *Nature* 387, 810-814 (1997).

8) Castillo, P. E., et al. Rab3A is essential for mossy fibre long-term potentiation in the hippocampus. *Nature* 388, 590-593 (1997).
9) D'Adamo, P., et al. DNA variants in the human RAB3A gene are not associated with autism. *Genes Brain Behav* 3, 123-124 (2004).
10) Ostermeier, C., Brunger, A, T. Structural basis of Rab effector specificity: crystal structure of the small G protein Rab3A complexed with the effector domain of rabphilin-3A. *Cell* 96, 363-374 (1999).
11) Pereira-Leal, J. B., Hume, A. N., Seabra, M. C. Prenylation of Rab GTPases: molecular mechanisms and involvement in genetic disease. *FEBS Letters* 498, 197-200 (2001).
12) Kobayashi, N., Mundel, P. A role of microtubules during the formation of cell processes in neuronal and non-neuronal cells. *Cell Tissue Res* 291, 163-174 (1998).
13) Kobayashi, N., et al. Process formation of the renal glomerular podocyte: is there common molecular machinery for processes of podocytes and neurons? *Anat Sci Internat* 79, 1-10 (2004).
14) Putaala, H., Soininen, R., Kilpeläinen, P., Wartiovaara, J., Tryggvason, K. The murine nephrin gene is specifically expressed in kidney, brain and pancreas: inactivation of the gene leads to massive proteinuria and neonatal death. *Hum Mol Genet* 10:1-8 (2001).
15) Ahola, H., et al. A novel protein, densin, expressed by glomerular podocytes. *J Am Soc Nephrol.* 14, 1731-7 (2003).
16) Beltran, P. J., Bixby, J., L., Masters, B. A. Expression of PTPRO during mouse development suggests involvement in axonogenesis and differentiation of NT3 and NGF-dependent neurons. *J Comp Neurol* 465, 384-395 (2003).
17) Gloy, J., et al. Amino acid transport in podocytes. *Am J Physiol Renal Physiol* 278, F999-F1005 (2000).
18) Mundel, P., et al. Synaptopodin: an actin-associated protein in telencephalic dendrites and renal podocytes. *J Cell Biol* 139, 193-204 (1997).
19) Peitsch, W., K., et al. Cell biological and biochemical characterization of drebrin complexes in mesangial cells and podocytes of renal glomeruli. *J Am Soc Nephrol* 14, 1452-63 (2003).
20) Kapfhamer, D., et al. Mutations in Rab3a alter circadian period and homeostatic response to sleep loss in the mouse. *Nat Genet* 32, 290-295 (2002).
21) Augustin, I., Rosenmund, C., Südhof, T. C., Brose, N. Munc-13 is essential for fusion competence of glutamatergic synaptic vesicles. *Nature* 400, 457-461 (1999).
22) Südhof, T. C. α-Latrotoxin and its receptors: neurexins and CIRL/latrophilins. *Annu. Rev. Neurosci.* 24, 933-962 (2001).
23) Takahashi-Iwanaga, H. Comparative anatomy of the podocyte: a scanning electron microscopy study. *Microsc. Res. Tech.* 57, 196-202 (2002).
24) Pavendstadt, H., Kriz, W., Kretzler, M. Cell biology of the glomerular podocyte. *Physiol Rev.* 83, 253-307 (2003).
25) Benzing, T. Signaling at the slit diaphragm. *J. Am. Soc. Nephrol.* 15, 1382-1391 (2004).
26) Bek, M., et al. Dopamine depolarizes podocytes via a D1-like receptor. *Nephrol. Dial. Transplant.* 14, 581-587 (1999).
27) Nitschke, R., et al. Acetylcholine increases the free intracellular calcium concentration in podocytes in intact rat glomeruli via muscarinic M(5) receptors. *J. Am. Soc. Nephrol.* 12, 678-687 (2001).
28) Kerjaschki, D., Farquhar, M. G. Immunocytochemical localization of the Heymann nephritis antigen (gp330) in glomerular epithelial cells of normal Lewis rats. *J. Exp. Med.* 157, 667-686 (1983).
29) Miyauchi, N., et al. Synaptic vesicle protein 2B (SV2B) interacts to slit diaphragm component and its decreased expression contributes to the development of proteinuria. *J. Am. Soc. Nephrol.* 15, 238A (abstract) (2004).
30) Yamagata, M., Sanes, R. J., Weiner, J. A. Synaptic adhesion molecules. *Curr. Opin. Cell Biol.* 15, 621-632 (2003).
31) Liu, G., et al. Neph1 and nephrin interaction in the slit diaphragm is an important determinant of glomerular permeability. *J. Clin. Invest.* 112, 209-221 (2003).
32) Reiser, J., Kriz, W., Kretzler, M., Mundel, P. The glomerula slit diaphragm is a modified adherens junction. *J. Am. Soc. Nephrol.* 11, 1-8 (2000).
33) Inoue, T., et al. FAT is a component of glomerular slit diaphragms. *Kidney Int.* 59, 1003-1012 (2001).
34) Benson, D. L., Colman, D. R., Huntley, G. W. Molecules, maps and synapse specificity. *Nat. Rev. Neurosci.* 2, 899-909 (2001).
35) Shen, K., Bargmann, C. I. The immunoglobulin superfamily protein SYG-1 determines the location of specific synapses in *C. elegans*. *Cell* 112, 619-630 (2003).
36) Donoviel, D. B., et al. Proteinuria and perinatal lethality in mice lacking NEPH a novel protein with homology to NEPHRIN. *Mol. Cell. Biol.* 21, 4829-4836 (2001).
37) Engert, F., Bonhoeffer, T. Dendritic spine changes associated with hippocampal long-term synaptic plasticity. *Nature* 399, 66-70 (1999).
38) Moolman, D. L., Vitolo, O. V., Vonsattel, J-P. G., Shelanski, M. L. Dendrite and dendritic spine alterations in Alzheimer models. *J. Neurocytol.* 33, 377-387 (2004).
39) Sanes, J. R., Lichtman, J. W. Development of the vertebrate neuromuscular junction. *Ann. Rev. Neurosci.* 22, 389-442 (1999).
40) McMahan, U. J. The agrin hypothesis. *Cold Spring Harbor Symp. Quant. Biol.* 55, 407-418 (1990).
41) Ilse Raats, C. J., et al. Expression of agrin, dystroglycan, and utrophin in normal renal tissue and in experimental glomerulopathies. *Am. J. Pathol.* 156, 1749-1765 (2000).
42) Mundel, P., Gilbert, P., Kriz, W. Podocytes in glomerulus of rat kidney express a characteristic 44 kD protein. *J. Histochem. Cytochem.* 39: 1047-1056 (1991).
43) Araque, A., Li, N., Doyle, R. T., Haydon, P. G. SNARE protein-dependent glutamate release from astrocytes. *J. Neurosci.* 20, 666-673 (2000).

REFERENCES FOR EXAMPLE 2

1) Kadota K, Kadota T. Isolation of coated vesicles, plain synaptic vesicles, and flocculent material from a crude synaptosome fraction of guinea pig whole brain. J Cell Biol. 1973 July; 58(1):135-51.
2) Rao A, Steward O. Evidence that protein constituents of postsynaptic membrane specializations are locally synthesized: analysis of proteins synthesized within synaptosomes. J Neurosci. 1991 September; 11(9):2881-95.
3) Chicurel M E, Terrian D M, Potter H. mRNA at the synapse: analysis of a synaptosomal preparation enriched in hippocampal dendritic spines. J Neurosci. 1993 September; 13(9):4054-63.
4) Cho W J, Jeremic A, Rognlien K T, Zhvania M G, Lazrishvili I, Tamar B, Jena B P. Structure, isolation, composition and reconstitution of the neuronal fusion pore. Cell Biol Int. 2004; 28(10):699-708.

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for treating podocyte injury associated with a nephropathy wherein the nephropathy is a renal glomerular disease selected from the group consisting of IgA nephropathy, Goodpasture's syndrome, Hereditary Nephritis, Alport Syndrome, Infection-related Glomerular Disease, Glomerulosclerosis, Diabetic nephropathy, Focal segmental glomerulosclerosis (FSGS), Membranous nephropathy, and Minimal change disease (MCD), said method comprising administering Brain Derived Neurotrophic Factor (BDNF) to an individual in need of treatment of the nephropathy.

2. A method according to claim 1, wherein the nephropathy is diabetic nephropathy.

3. The method of claim 1 wherein the nephropathy occurs during a disease selected from the group consisting of diabetes, hypertension, and Systemic lupus erythematosus (SLE).

4. The method of claim 1 wherein the nephropathy is an Infection-related Glomerular Disease selected from the group consisting of acute post-streptococcal glomerulonephritis (PSGN)-related Glomerular Disease, bacterial endocarditis-related Glomerular Disease, and HIV-related Glomerular Disease.

* * * * *